(12) United States Patent
Shi et al.

(10) Patent No.: US 12,415,019 B2
(45) Date of Patent: *Sep. 16, 2025

(54) BIOFLEXIBLE ELASTOMER INTESTINAL ANASTOMOSIS STENT BASED ON PTMC-b-PEG-b-PTMC COPOLYMER, AND PREPARATION METHOD

(71) Applicant: WENZHOU INSTITUTE, UNIVERSITY OF CHINESE ACADEMY OF SCIENCES, Wenzhou (CN)

(72) Inventors: Changcan Shi, Wenzhou (CN); Xujian Li, Wenzhou (CN); Luqi Pan, Wenzhou (CN); Zhixiao Ji, Wenzhou (CN); Xiao Yang, Wenzhou (CN)

(73) Assignee: WENZHOU INSTITUTE, UNIVERSITY OF CHINESE ACADEMY OF SCIENCES, Zhejiang (CN)

( * ) Notice: Subject to any disclaimer, the term of this patent is extended or adjusted under 35 U.S.C. 154(b) by 0 days.

This patent is subject to a terminal disclaimer.

(21) Appl. No.: 18/552,411

(22) PCT Filed: Apr. 25, 2022

(86) PCT No.: PCT/CN2022/088874
§ 371 (c)(1),
(2) Date: Sep. 25, 2023

(87) PCT Pub. No.: WO2022/228357
PCT Pub. Date: Nov. 3, 2022

(65) Prior Publication Data
US 2024/0100228 A1    Mar. 28, 2024

(30) Foreign Application Priority Data

Apr. 30, 2021    (CN) .......................... 202110487844.3

(51) Int. Cl.
| | | |
|---|---|---|
| *A61L 31/14* | (2006.01) | |
| *A61L 31/06* | (2006.01) | |
| *A61L 31/16* | (2006.01) | |
| *C08G 64/18* | (2006.01) | |
| *D01F 1/10* | (2006.01) | |
| *D01F 6/94* | (2006.01) | |

(52) U.S. Cl.
CPC ............. *A61L 31/06* (2013.01); *A61L 31/148* (2013.01); *A61L 31/16* (2013.01); *C08G 64/183* (2013.01); *D01F 1/103* (2013.01); *D01F 6/94* (2013.01); *A61L 2300/202* (2013.01); *A61L 2300/404* (2013.01)

(58) Field of Classification Search
CPC . C08G 64/183; A61L 2300/202; D01F 1/103; D01F 6/94
See application file for complete search history.

(56) References Cited

U.S. PATENT DOCUMENTS

| 8,048,168 | B2 | 11/2011 | Dillinger | |
|---|---|---|---|---|
| 8,445,603 | B2 | 5/2013 | Schwartz et al. | |
| 9,205,179 | B2 | 12/2015 | Priewe et al. | |
| 2006/0178739 | A1* | 8/2006 | Shalaby | A61F 2/90 623/1.49 |
| 2006/0212050 | A1* | 9/2006 | D'Agostino | A61B 17/072 606/151 |
| 2008/0114466 | A1 | 5/2008 | Shelton | |
| 2013/0261736 | A1 | 10/2013 | Kleiner | |
| 2015/0051687 | A1* | 2/2015 | Dickerhoff | A61F 2/86 623/1.11 |

FOREIGN PATENT DOCUMENTS

| CN | 101133973 | A | 3/2008 |
|---|---|---|---|
| CN | 103239265 | A | 8/2013 |
| CN | 109480943 | A | 3/2019 |
| CN | 111449707 | A | 7/2020 |
| CN | 113413491 | A1 | 9/2021 |

(Continued)

OTHER PUBLICATIONS

CN101133973, (machine translation) Stomach and Intestine Inosculated Bracket and Method for Preparing the Same, (May 3, 2008), pp. 1-5 (Year: 2008).*

Han, Jie et al., Carbohydrate Polymers 79 (2010) pp. 214-218 (Year: 2010).*

Ajiro, Hiroharu, et al., "Polymer design using trimethylene carbonate with ethylene glycol units for biomedical applications," *Polymer Journal*, vol. 48, No. 7, pp. 751-760 (Apr. 2016).

Wu, Lei, et al., "Bioabsorbable flexible elastomer of PTMC-b-PEG-b-PTMc copolymer as intestinal anastomosis scaffold," *Polymers for Advanced Technologies*, vol. 32, No. 2, pp. 3633-3645 (May 11, 2021).

(Continued)

*Primary Examiner* — Brian-Yong S Kwon
*Assistant Examiner* — Lyndsey M Beckhardt
(74) *Attorney, Agent, or Firm* — Christensen, Fonder, Dardi & Herbert PLLC; John P. Fonder

(57) ABSTRACT

A bioflexible elastomer intestinal anastomosis stent based on a PTMC-b-PEG-b-PTMC copolymer, and a preparation method. Biocompatible degradable polymer medical materials, i.e., PTMC and PEG, are selected, an electrostatic spinning method is used for preparation, the size of an anastomosis tube can be adjusted according to the size of a human lumen, and the anastomosis tube is designed to not only be suitable for an anastomat of the small intestines and large intestines, but also suitable for an anastomotic and pre-supported lumen anastomat of an esophagus, artery, vein, etc. The anastomosis tube prepared has a thin wall and excellent elasticity, and in order to facilitate suturing by a doctor during a clinical surgical operation, the anastomosis tube is innovatively and seamlessly sleeved outside a plant cellulose tube having high hardness.

16 Claims, 10 Drawing Sheets

(56) References Cited

FOREIGN PATENT DOCUMENTS

| | | |
|---|---|---|
| DE | 199 26 008 A1 | 12/2000 |
| JP | 2009-539548 A | 11/2009 |
| JP | 2012-503092 A | 2/2012 |
| JP | 2014-528954 A | 10/2014 |
| JP | 2015-530157 A | 10/2015 |

OTHER PUBLICATIONS

Wang, Hong, et al., "Synthesis and Characterization of ABA-Type Block Copolymer of Poly(trimethylene carbonate) with Poly(ethylene glycol): Bioerodible Copolymer," *Journal of Polymer Science Part A: Polymer Chemistry*, vol. 36, No. 5, pp. 695-702 (Apr. 15, 1998).

Wang, H., et al., "Studies on Properties and Drug Delivery Systems of PTMC-b-PEG-b-PTMC Block Copolymers," *Journal of Micromolecular Science, Part A: Polymer Chemistry*, vol. 35, No. 5, pp. 811-819 (May 31, 1998).

\* cited by examiner

BIOFLEXIBLE ELASTOMER INTESTINAL ANASTOMOSIS STENT BASED ON PTMC-b-PEG-b-PTMC COPOLYMER, AND PREPARATION METHOD

RELATED APPLICATIONS

The present application is a National Phase entry of PCT Application No. PCT/CN2022/088874, filed Apr. 25, 2022, which claims priority to Chinese Patent Application No. 202110487844.3, filed Apr. 30, 2021, the disclosures of which are hereby incorporated by reference herein in their entirety.

TECHNICAL FIELD

The present disclosure specifically relates to the technical field of polymer materials, and specifically relates to a bioflexible elastomer intestinal anastomosis stent based on PTMC-b-PEG-b-PTMC copolymer and a preparation method thereof.

BACKGROUND OF THE INVENTION

Gastrointestinal reconstruction anastomosis is one of the most common surgical procedures in abdominal surgery. In the past century of the development of gastrointestinal surgery, the incidence of anastomotic fistula has not decreased significantly, which has become one of the worldwide challenges to the success rate of gastrointestinal surgery. Intestinal lesions such as gastrointestinal benign and malignant tumors, gastrointestinal perforation, gastrointestinal obstruction, hemorrhage and ischemia, often require resection of part of the diseased intestinal tract before anastomosis. Traditional methods mostly use manual suture anastomosis. In recent decades, most use tubular stapler for end-to-end or end-to-side anastomosis, or linear cutter stapler for side-to-side anastomosis. Regardless of the anastomosis procedure, anastomotic fistula, a deadly complication, cannot be prevented.

At present, it is generally accepted and practiced by colorectal surgeons at home and abroad that temporary bypass surgery, such as temporary ileostomy or colostomy and other additional surgeons, can definitely avoid the complications caused by anastomotic fistula, but there is no literature to support whether it can reduce the occurrence probability of anastomotic fistula. However, the bypass surgery requires planned reoperation for reversion, and re-reversion also means re-gastrointestinal reconstruction and anastomosis. There is also the occurrence probability of anastomotic fistula, anastomotic stenosis and other related complications, but the occurrence probability is lower than that of the first operation. Achieving isolation of intestinal contents, especially fecal contents, in the area of the anastomotic stoma with good blood supply at both ends of the anastomotic stoma and without tension in apposition, and achieving relative isolation and a clean local environment is an effective strategy to prevent anastomotic fistula and complications such as peritonitis and abdominal abscess. The key technical bottleneck of realizing the strategy is the breakthrough of ideal auxiliary anastomosis material.

The purpose of intestinal anastomosis is to restore the physical, histological and physiological function of the intestine at both ends of the anastomotic stoma. At present, the main problems of the conventional stapler include that: (1) metal staplers are not biodegradable, resulting in permanent retention in the body; (2) degradable high molecular material staplers lack mechanical matching with wound tissue; (3) the staplers lack the regulation and control function of tissue repair, and cannot reasonably regulate and control the recovery of normal intestinal function. Patent of invention CN 111449707A proposes an anorectal stapler, including a handle base, a transmission assembly, a percussion assembly and a anastomosis-cutting assembly; the transmission assembly includes a screw rod arranged inside a handle seat and an adjustment mechanism arranged at a tail end of the handle seat and connected a the tail end of the screw rod; a nailing seat is fixedly mounted on a front end of the lead screw; the percussion assembly includes a movable handle provided on the handle seat and a straight push rod sheathed on the lead screw; the anastomosis-cutting assembly includes a staple pusher, a cartridge housing, a cartridge, and a circular knife. In this disclosure, the staple pusher, the staple cartridge sleeve and the staple cartridge are made of metal materials, and the components cannot be degraded in vivo, and can only be permanently retained in vivo or removed by secondary surgery. Patent CN109480943 A is made of degradable materials, adopts the method of nail body perforation and fixation, and designs a support frame at a rear end of the nail body. However, the anastomotic ring has large stiffness and inelasticity, and cannot well adapt to intestinal peristalsis, with obvious foreign body sensation. Similarly, there is a patent of invention CN 103239265 A, in which the degradable materials polyglycolide and polylactide are used as raw materials for gastrointestinal anastomosis. The stapler has the function of fragile disassembly, but also lacks the mechanical matching with intestinal tissue. An ideal stapler should have the following characteristics: (1) effective isolation of intestinal contents; (2) the operation of stapler implantation having little damage to the intestinal wall of anastomosic stoma; (3) being easy to operate. The stapling devices currently on the market do not meet the above-mentioned requirements at the same time.

From a production standpoint, stents must be easily manufactured in a variety of different lengths and diameters to accommodate different individuals and do not require any complicated storage procedures. All must meet the requirements while maintaining the economy and affordability of the stent.

SUMMARY OF THE INVENTION

In order to solve the technical defects existing in the prior art, the present disclosure provides a bioflexible elastomer intestinal anastomosis stent based on PTMC-b-PEG-b-PTMC copolymer and a preparation method thereof, which has the functions of matching intestinal elasticity, regulating and controlling tissue repair, and can significantly reduce the occurrence probability of intestinal anastomotic fistula and other complications.

The technical solution adopted by the present disclosure is a bioflexible elastomer intestinal anastomosis stent based on PTMC-b-PEG-b-PTMC copolymer, wherein the intestinal anastomosis stent is integrally made of a PTMC-b-PEG-b-PTMC copolymer material, and the PTMC-b-PEG-b-PTMC copolymer is a triblock PTMC-b-PEG-b-PTMC copolymer synthesized by ring-opening polymerization method of high-molecular medical materials of PTMC and PEG; a content of PEG in the PTMC-b-PEG-b-PTMC copolymer is 10%-20%, and a thickness of the intestinal anastomosis stent is 0.05-0.3 mm.

The PTMC-b-PEG-b-PTMC copolymer material of the bioflexible elastomer intestinal anastomosis stent is loaded with triclosan (TCS).

A plant cellulose tube sleeve is further provided in the intestinal anastomosis stent, the intestinal anastomosis stent is of a gapless sleeve-in-type structure, an inside is a tube of plant cellulose material, and an outside is the PTMC-b-PEG-b-PTMC copolymer material.

A preparation method of a bioflexible elastomer intestinal anastomosis stent, which is prepared via the following steps:
(1) ring-opening polymerization of PTMC-b-PEG-b-PTMC: transferring PEG and TMC monomers into a reaction vessel, dissolving catalyst $Sn(Oct)_2$ in an anhydrous toluene solution under a $N_2$ atmosphere, adding 100 ppm to the reaction vessel with a pipette for copolymerization to ensure that the whole process is anhydrous and oxygen-free, dissolving a product after 24 h, and purifying a polymer solution after complete dissolution, repeating for multiple times, and drying the purified copolymer in a vacuum drying oven for 48 h, and then storing same in a drying cabinet;
(2) preparation of an anastomotic stent by electrospinning: dissolving the dried sample in a DMF/THF mixed solution, the prepared solution having a concentration of 5-10.0%, adding 0.1-1.0 wt % of an antibacterial agent into the mixed solution; after mixing, placing same on a shaker at 37° C. for sufficient dissolution of the sample to obtain a uniform co-dissolved spinning stock solution; loading the stock solution into a 2.5 ml of syringe, the syringe including a metal needle with an inner diameter of 0.5 mm, and the sample having a thickness of 0.2±0.01 mm after spinning; and further drying the obtained fibre in the vacuum drying oven at room temperature to remove residual organic solvents and moisture.

In the step (1), the TMC monomer is 70-90 wt %, the PEG is 5-29 wt %, and the catalyst $Sn(Oct)_2$ solution is 1-5 wt %.

The copolymerization in the step (1) is carried out at conditions of a temperature of 100-150° C. and a reaction time of 24-48 h.

In the step (1) the product is dissolved at a condition that $CHCl_3$ or DMF or THE is used for dissolution, the product being placed on a shaker, a temperature of the shaker being set at 37° C.

The purification in the step (1) is performed at a condition that the purification is performed with n-hexane or ethanol and stirring is continuously performed with a glass rod.

The DMF:THF=1:1 in the mixed DMF/THF solution of step (2).

The spinning step of step (2) is specifically that a plant cellulose tube sleeve of a certain size is sheathed on an electrospinning receiver for spinning, and a tube of a corresponding size is able to be obtained by controlling parameters, a needle pushing speed V=1.0-5.0 ml/h, a rotation speed of a roller V=100-500 RPM, a temperature T=25-35° C., and a humidity WET=20-40%.

Advantageous effects of the present disclosure are that the present disclosure provides a bio-flexible elastomeric intestinal anastomosis stent based on PTMC-b-PEG-b-PTMC copolymer and preparation method thereof, wherein biocompatible degradable polymer medical materials PTMC and PEG are selected and prepared via electrospinning method, a dimension of a anastomosis tube can be adjusted according to a size of human lumen, the anastomosis tube being designed to be suitable not only for staplers of small intestine and large intestine, but also for lumen staplers of esophagus, artery and vein anastomosis and pre-supports, the anastomosis tube prepared in the present disclosure has thin wall and excellent elasticity, so as to facilitate the suturing by doctors in clinical surgery, innovatively inserting the anastomosis tube seamlessly outside a plant cellulose tube with greater stiffness. The plant cellulose is commercially available, can play a supporting role in suture, and is convenient to operate. In the intestinal environment, after 15-30 min, it can be completely decomposed and discharged outside the body, without affecting the performance of subsequent anastomotis tube. At the same time, the degradable intestinal anastomotis tube has the function of tissue microenvironment regulation by loading different functional factors of antibacterial, anti-inflammatory and regulating fibroblast proliferation and migration, so as to regulate the microenvironment of anastomotic site and reduce the probability of anastomotic fistula. The stent is generally degraded in vivo for 2-3 weeks and excreted from the body through intestinal tract, which can make up for the non-degradable defect of metal device and has excellent tissue compliance, which makes up for the lack of tissue compliance of degradable anastomosis device. Subsequent characterization also demonstrates that the degradable anastomosis tube has certain advantages in reducing postoperative anastomotic bleeding, reducing postoperative anal discomfort, gastrointestinal dysfunction, and reducing medical costs, especially in the absence of foreign body residues at the anastomosis.

DETAILED DESCRIPTION OF THE INVENTION

Figure 1:
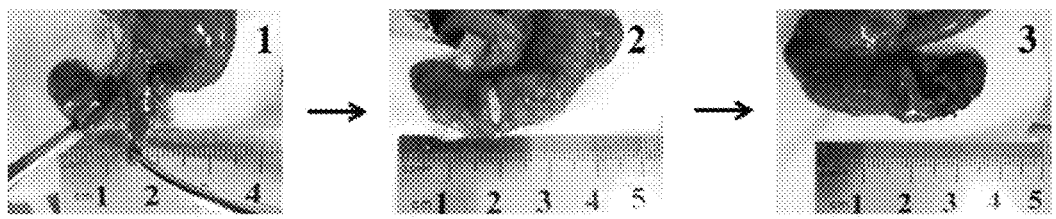
FIG. 1 is an in vivo experimental procedure; (1) Cecal incision; (2) Implantation of anastomosis stent; (3) Interrupted full-thickness suture.

The embodiments of the present disclosure will now be described more clearly and fully hereinafter with reference to the accompanying drawings, in which embodiments of the disclosure are shown. It is to be understood that the embodiments described are only a few, but not all embodiments of the disclosure. Based on the embodiments of the present disclosure, all other embodiments obtained by a person of ordinary skill in the art without inventive effort fall within the scope of the present disclosure.

Materials

Poly (ethylene glycol) (PEG, mn=5000), stannous octoate ($(Sn(Oct)_2)$), tetrahydrofuran (THF), N-dimethylformamide (DMF), trichloromethane ($CHCl_3$), triclosan (TCS), toluene, n-hexane, lipase (Lipase from *Aspergillus oryzae*; solution, ≥100,000 U/g) are purchased from Sigma-Aldrich Co. LLC. Polymer grade 1,3-trimethylene carbonate (TMC, Daigang Biology, China). All reagents and chemicals are of analytical grade and are used without further purification.

The mouse fibroblast cell line L929 was provided by the Center for Type Culture Collection, Chinese Academy of Sciences (Shanghai, China). Culture dishes were purchased from Corning Inc. (New York, USA). Dulbecco's modified Eagle medium (DMEM, Gibco) is supplemented with 10% fetal bovine serum (FBS, Gibco), 100 IU/ml of penicillin and 100 mg/ml of streptomycin sulfate. Cultures are performed All cells are cultured in a 37° C., 5% $CO_2$, fully humidified incubator.

Male Sprague-Dawley rats (200±20 g) provided by the Laboratory Animal Center of Wenzhou Medical University (Wenzhou, China) are cultured under the conditions of 25° C. and 55% humidity. All animal experiments are performed in accordance with guidelines assessed and approved by the Ethics Committee.

Preparation Step of Intestinal Anastomosis Stent Taking PTMC-b-PEG-b-PTMC as a Base Material Ring-Opening Polymerization of PTMC-b-PEG-b-PTMC Triblock PTMC-b-PEG-b-PTMC copolymer is synthesized via ring-opening polymerization. Briefly, metered amounts of PEG and TMC are transferred to a completely dry glass reactor with a magnetic stirring rod. $Sn(Oct)_2$ is dissolved in anhydrous toluene solution under $N_2$ atmosphere and 100 ppm is added to the reaction vessel with a pipette. The copolymerization is carried out at 130±2° C. for 24 h to ensure that the whole process is free of water and oxygen. After 24 h, the product is dissolved in chloroform. After complete dissolution, the polymer solution is purified with an excess of n-hexane for 3 times. The purified copolymer is dried in a vacuum oven at 40° C. for 48 h and then stored in a drying cabinet.

Preparing Anastomosis Stent by Electrospinning

The dried sample is dissolved in a mixed solution of DMF/THF (1/1, V/V) to prepare a solution with a concentration of 10.0%, and placed on a shaker at 37° C. for 36 h to sufficiently dissolve the sample, so as to obtain a uniform co-dissolved spinning stock solution. The stock solution is loaded into a 2.5 ml of syringe comprising a metal needle with an internal diameter of 0.5 mm. Specific spinning conditions are based on previous laboratory experience and are detailed in Table 1 for support materials. The sample thickness after spinning is 0.2±0.01 mm. The resulting fibers are further dried in a vacuum drying oven at room temperature for 24 hours to remove residual organic solvents and moisture. The spun samples are used for mechanical property testing as well as in vitro degradation testing.

The particular preparation method is as follows:

1. Synthesis of mPEG-PTMC: the synthetic process needing to be operated in an anhydrous and oxygen-free environment, adding a solution of 70-90 wt % of TMC monomer, 5-29 wt % of PEG5000 and 1-5 wt % of catalyst $Sn(Oct)_2$ into a reaction tube, placing a magneton in the reaction tube, sealing a tube opening with silicone grease after ensuring that the reaction tube is anhydrous and oxygen-free, sealing the tube opening with a sealing film to ensure that no oxygen and moisture enter; placing the reaction tube into an oil bath for a reaction, a temperature being 100-150° C., a reaction time being 24-48 h, and after the reaction is finished, taking out the solution for use 2. Dissolution of mPEG-PTMC: according to a solid-liquid ratio of 1:5, using CHCl3 or DMF or THE to dissolve the synthesized material; first washing the inner wall with $CHCl_3$ or DMF or THE for a plurality of times, washing away silicone grease and unreacted monomers, then adding an excess of $CHCl_3$ or DMF or THF, placing the solution on a shaker, a temperature of the shaker being set at 37° C., and waiting for the solution to completely dissolve.

3. Purification of mPEG-PTMC: the dissolved solution being slowly poured into a beaker containing n-hexane or ethanol for purification, slowly poured and continuously stirred with a glass rod; the obtained flocculent mPEG-PTMC being suction-filtered, followed by drying in a vacuum drying box for 48 h.

4. Preparation of electrospinning solution: the synthetic material mPEG-PTMC is dissolved in the solvent DMF/THF (DMF:THF=1:1), and the mass fraction of the solution is 5-10 wt %. The mass of the antimicrobial agent added is based on 0.1-1.0 wt % of the material added. The polymer mPEG-PTMC, the antimicrobial agent and both solvents are mixed and the prepared solution is placed on a constant temperature shaker at 37° C. for 24 h until complete dissolution. After dissolution is complete, the spinning operation is performed.

5. Preparation of anastomosis tubes by electrospinning: spinning was performed on an electrospinning model TL-Pro-BM. A plant cellulose tube sleeve of a certain size is sheathed on an electrospinning receiver for spinning, and a tube of a corresponding size is able to be obtained by controlling parameters. The anastomosis tube obtained by electrospinning is a two-part gapless sleeve-in-type structure with a tube of plant cellulose material inside and a tube of synthetic polymer material outside. The parameters are set in the ranges of a voltage of (−5, 30) V; a needle push speed of V=1.0-5.0 ml/h; a roller speed of V=100-500 RPM; a temperature of T=5-35° C.; a humidity of WET=20-40%.

TABLE 1

Electrospinning conditions

| Needle pushing speed (mL/h) | Distance from needle to receiver (cm) | Rotation speed of roller (RPM) | Voltage range (V) | Temperature (° C.) | Humidity (%) |
|---|---|---|---|---|---|
| 0.9 | 20 | 400 | −1.20 | 35 | 25 |

Characterization
Physicochemical Characterization

The FTIR-ATR spectra of the polymers PTMC, PEG and the block copolymer PTMC-b-PEG-b-PTMC are measured with a Nicolet Magna-560 spectrometer equipped with an ATR accessory. The $^1$H-NMR spectra of PTMC and the block copolymer PTMC-b-PEG-b-PTMC are measured with a Bruker spectrometer. All $^1$H-NMRs take tetramethylsilane (TMS) as internal reference and deuterated chloroform ($CDCl_3$) as solvent, and record chemical shifts in ppm as unit.

Hitachi cold field emission electron microscope SU8010 field emission scanning electron microscope is used to photograph the micro-morphology of the sample after electrospinning and the micro-morphology after degradation in the implanted animals.

The thermal properties of the polymers PTMC, PEG and the block copolymer PTMC-b-PEG-b-PTMC are recorded with DSC analysis using DSC8000 (PerkinElmer, USA) at a ramp rate of 10° C./min.

The dynamic contact of samples with different PEG contents are measured at 37° C. using a Biolin Theta type dynamic contact angle analyzer, and the contact angle size is recorded every 5 min until being stable.

The intrinsic viscosity of PTMC-b-PEG-b-PTMC is determined using an ubbelohde viscometer in a thermostatic water bath at 25° C., the solvent being phenol/1,1,2,2-tetrachloroethane (2/3, W/W), and the test results are the average of three experiments. The viscosity average molecular weight of the polymer is calculated by the Mark-Houwink equation:

$$[\eta] = KM_v^\alpha, \quad M_v = \left(\frac{[\eta]}{K}\right)^{\frac{1}{\alpha}}$$

where $K=7.9 \times 10^{-2}$ cm$^3$/g, $\alpha=0.63$.

The mechanical properties are tested on an electronic universal material testing machine (Instron5944). The sample after electrospinning is treated as sheet material with the size of 45.0 mm×25.0 mm×0.2 mm, and the size of SD rat cecum is 45.0 mm×25.0 mm×0.3 mm. The sample is rinsed with normal saline, and the excess water on the surface is wiped off.

Fiber Diameter and Porosity of Stent

At least 20 fibers and 50 fragments are measured in one scanning electron microscope image to obtain the average diameter and diameter distribution of the fibers, and the porosity of the stent is calculated using the following equation:

$$P = \left(1 - \frac{\rho'}{\rho_0}\right)$$

where P is the porosity of the stent, p' is an apparent density of the stent and $\rho_0$ is a bulk density of the copolymer.

Water Absorption

A sample with an initial weight of about 40 mg ($W_0$) swelled in PBS (37° C.). After 24 hours, excess surface moisture is removed with filter paper and the swollen sample mass ($W_s$) is reweighed. The water absorption of the sample is determined by the following equation:

$$\text{Water absorption} = (W_s - W_0)/W_0 \times 100\%$$

Bio-Degradability

A PTMC-b-PEG-b-PTMC film with the size of 10.0×10.0×0.2 mm is taken, placed in 1 mL of lipase solution with an air bath at 37° C., and shaken for 8 h each day, with an amplitude of 65 times/min. The enzyme solution is changed every 3 days to maintain enzyme activity, samples are taken after 1, 5, 10, 15 and 20 days respectively, and 3 parallel strips are randomly taken. After the sample is sufficiently washed with distilled water, the filter paper suctions the surface moisture and dries it in vacuum at 37° C. for 12 h to constant mass. The mass of the dried sample and the pH of the medium containing degradation products are recorded.

In vivo bio-degradation behavior is obtained by recording the mass and size of anastomosis stent before and after implantation. After taking out the anastomosis stent, distilled water is used to clean it, and the filter paper is suctioned to dry the surface moisture. The weight loss rate is calculated by the following formula $$\text{Weight loss } (\%) = (W_0 - W_t)/W_0 \times 100\%$$

where $W_0$ and $W_t$ represent the dry weight of the sample before and after degradation, respectively.

Biological Characterization
Hemolysis Study of Copolymer

Hemolysis rates are used to evaluate hemocompatibility of hemoglobin films. Extracts of PHMs are obtained by immersing 20 mg of sample in 9 ml of normal saline and incubating (37° C.) for 24 hours according to previously reported methods. Two hundred microliters of fresh anticoagulant blood is injected into one milliliter of the extract and mixed well. After incubation (37° C.) for 1 hour, the mixture of anticoagulant blood and extract is centrifuged (3000 rpm, 10 min). Finally, the absorbance (545 nm) of the supernatant is measured using a mixed multi-mode microplate reader (Synergy NEO2, BioTek, USA). Ultrapure water and normal saline are used as negative and positive controls, respectively. Hemocompatibility is expressed as hemolysis (%) as follows:

The sample material is previously rinsed with distilled water, wiped clean to indicate excess moisture, and human whole blood is used. Experimental group: 15 mg of the electrospun sample is taken and placed in an EP tube, added with 1 mL of normal saline and 0.1 mL of whole blood, negative control group: 1 mL normal saline and 0.1 mL whole blood are added into EP tube, positive control group: the EP tube is filled with 1 mL of ultrapure water and 0.1 mL of whole blood. All the samples are incubated at 37° C. for 2 h for hemolysis test.

All test samples are centrifuged at 3000 rpm for 10 minutes repeated if the supernatant is not clear. After photographing, the supernatant is aspirated and transferred into a well plate, three parallel samples are prepared of the supernatant of each sample, 200 μL of each sample is transferred, the absorbance (OD) is absorbed at 540 nm of wavelength with 721 spectrophotometer and the results are recorded.

Data processing: the mean values of OD of 3 samples in sample group and control group are taken, respectively. The hemolysis rate of the sample is calculated according to the formula.

$$H(\%) = \frac{ODt - ODnc}{ODpc - ODnc} \times 100\%$$

where H % is the hemolysis rate, $OD_t$ is the absorbance of sample, $OD_{nc}$ is the absorbance of negative control sample and $OD_{pc}$ is the absorbance of positive control sample. According to GB/T1423.2-1993 standard, through the determination of erythrocyte lysis and hemoglobin free degree caused by the material in contact with red blood cells in vitro, the in vitro hemolysis of the material is evaluated, and the hemolysis reaction of more than 5% is positive.

Cytotoxicity Study

First, a cell suspension (100 μL) at a density of $5 \times 10^4$ cells is added to each well of a 96-well plate and incubated at 37° C. in an atmosphere of 5% $CO_2$ in air for 24 hours for cell attachment. The media is then replaced with the sample extract (100 mL) and incubated for 24 hours and 48 hours. Thereafter, the CCK-8 assay is performed by adding CCK-8 solution (10 ml, 10% in complete medium) to each well and incubating for an additional 2 hours at 37° C. and 5% $CO_2$. Absorbance is measured at 450 nm with a microplate reader. Cells without any treatment are used as blanks.

CCK-8 method is used for toxicological study of test samples, and the test procedures are as follows:

Preparation of cell culture solution: RPMI1640 medium of 500 mL+fetal bovine serum of 50 mL+penicillin/streptomycin double antibody of 5 mL.

Preparation of extract of test group: the samples are sterilized with 75% alcohol prior to ultra-clean bench ultraviolet irradiation for 30 min on both sides. The electrospun samples are cut into square films with a side length of 1.82 cm, added with 2 mL of complete medium, and performed with a bathing at 37° C. for 24 hours to obtain the extract of the electrospun sample.

Cell preparation: the cell culture liquid is used to culture L929 cells (adherent cells) in vitro, proliferate for more than 3 generations, and then reach the culture flask. Three times are rinsed with PBS (do not face the cells to prevent cells from being washed out). It is then digested with 0.25% trypsin for 30 s (37° C.) to become a cell suspension. 3-5 mL of complete medium is immediately added and transferred to centrifuge tube, centrifuged at 1000 rpm for 5 min, the upper waste liquid is discarded, 5 mL of PBS is added to the centrifuge tube, and the pipette is purged to evenly disperse the cells. 1 μL is added to the counting plate for cell counting, and the cell concentration is adjusted to $5 \times 10^4$ cells/mL.

Co-culture: the diluted L929 cells are seeded in a 96-well plate at 100 μL per well, and 5000-8000 cells are required per well; after 24 hours of culture at 37° C. and 5% $CO_2$, the cells are completely adherent and the culture solution is discarded. 100 μL per well of the extract from the experimental group and the positive solution (10% DMSO (200 μL) for the positive control group) are added into each group of 6 replicate wells and incubated at 37° C. in an incubator for 24 h.

CCK-8 assay: the 96-well plate is taken out at preset time points (24 h and 48 h), the stock solution is sunctioned out and added around the sample well, 10 μL of CCK-8 reagent and 100 μL of complete medium are respectively added into each well (firstly the two solutions are mixed), incubated in the incubator at 37° C. for 2 h, and then a multi-functional microplate reader (absorbance of 450 nm) was used to detect the absorbance (OD) value.

Calculation of relative growth rate: the mean value of OD value of 6 wells are taken for each group, and the relative growth rate (RGR) of each group according to the following formula:

$$\text{Cell Viability (\%)} = \frac{As - Ab}{Ac - Ab} \times 100\%$$

wherein $A_s$ is an absorbance of a test well (with polymer extract, cell culture medium and CCK-8);
$A_c$ is an absorbance of a control well (without polymer extract, with cell culture medium and with CCK-8);
$A_b$ is an absorbance of an experimental well (without polymer extract, without cell culture medium, with CCK-8).

Antibacterial Study

50 μL of bacterial stock solution of frozen *Escherichia coli* and *Staphylococcus aureus* are respectively added into a centrifuge tube filled with 5 mL of bacterial culture solution, and incubated in a bacterial incubator for 24 h before use. The material is cut into circular sheet material with a diameter of 1.0 cm, the excess moisture on the surface is wiped out with 75% alcohol and then cleaned, and ultraviolet disinfection is performed for 30 min. 100 μL of diluted bacteria is respectively taken and evenly coated on the culture medium, the circular plate material is placed on the culture medium coated with bacteria and incubated in a bacterial incubator at 37° C. for 24 h.

In Vivo Bio-Compatibility Studies

SD Rat In Vivo Assay

Prior to test, the sample is soaked with 75% alcohol for 10 min, and performed with ultraviolet sterilization for 30 min. 180 general grade Sprague-Dawley male rats weighing 200±10 g are anesthetized with 10% chloral hydrate by intraperitoneal injection according to body weight. The experiment is provided with three groups, i.e., PTMC-b-PEG-b-PTMC group, TCS/PTMC-b-PEG-b-PTMC group and blank control. Four time points are set up in each group, i.e. 7 days, 14 days, 21 days and 28 days respectively. Parallel group is set up with 5 rats. The rat abdomen is shaved, the abdomen is opened, and the rat cecum is exposed. The incision is made at the middle and upper part of the cecum, with the size of 10±1 mm. The contents of the cecum are cleaned. The PTMC-b-PEG-b-PTMC group and the TCS/PTMC-b-PEG-b-PTMC group are placed in the experimental sample and then sutured. The blank group is sutured directly without material. Four-needle simple interrupted full-thickness suture is used for the suture of anastomotic site. Taking the cross section of cecum as the object, full-thickness interrupted suture is performed at 3, 6, 9 and 12 positions corresponding to the clock positions, with the needle distance of about 0.4 cm and the spacing of about 0.5 cm. The rats in both groups are given food and water ad libitum immediately after anesthesia.

After operation, each rat is kept in one cage independently, and the food intake, defecation and behavior are closely observed. The postoperative general conditions and death are recorded in three groups. After reaching the corresponding time point, rats in each group are anesthetized and performed with laparotomy, abdominal adhesion condition, whether there is abdominal infection and whether there is anastomotic fistula observed and recorded.

Abdominal Adhesion Score (Adhesion Score)

The postoperative abdominal adhesions of SD rats are graded and quantified to obtain a quantified result. Scoring criteria are (0-3 points):

0 Point: no adhesion;
1 Point: mild adhesion, tissue covering only vicinity of the anastomotic stoma which is easy to separate;
2 Points: moderate adhesion, adhesion occurring between the anastomosis site and intraperitoneal tissue, which is difficult but still possible to separate;
3 Points: severe adhesion, the anastomotic stoma being surrounded by abdominal tissue or other organ tissue adhesion.

Anastomotic Burst Pressure

The burst pressure of anastomotic tissue is an important mechanical indicator to detect the healing strength of anastomotic stoma, which reflects the amount of pressure the intestinal tract can bear and is commonly used to detect the healing strength of anastomotic stoma.

On postoperative day 7, burst pressure test is performed on the intestinal segment of anastomotic stoma using in vitro manometry. The anastomotic stoma and about 5 cm intestinal tube around it are cut off, the intestinal contents are flushed out of the intestinal tract with normal saline. The abdominal adhesions are appropriately separated, the intestinal segment at each anastomotic site is expose, one end of intestinal tube is connected with a pressure gauge (YB-150A precision pressure gauge), two wires are used for bundling and fixing, and also two wires are used to ligate and close the intestinal cavity across the other end of anastomotic stoma, so that the intestinal tube and pressure gauge are at the same level. A peristaltic pump is used to uniformly inject methylene blue diluent (0.16 mg/mL) into the intestinal tube at the speed of 10 mL/min, attention is paid to observe the anastomotic stoma, and the reading is recorded on the pressure gauge when there is blue liquid overflow (or sudden pressure drop) at the anastomotic stoma, which is the burst pressure of anastomotic stoma.

H&E Staining

Anastomotic tissues are fixed in 4% formaldehyde solution, embedded in conventional paraffin, and sectioned at 4 μm. Sections are conventionally deparaffinized with xylene, washed with various levels of ethanol, drained with the slide and placed in hematoxylin solution to be stained for 4 min. Differentiated with 1% hydrochloric acid ethanol, the sections return to blue for about 30 min in weak alkaline water, rinsed with running water for 5-10 s, and then placed into anhydrous ethanol glass jar for stirring and shaking for 30 s, then the slide is drained and placed into eosin staining solution. The stained sections are observed by light microscopy.

Masson Stain

The tissues are fixed in 10% neutral formalin solution, washed in running water and routinely dehydrated and embedded. Iron hematoxylin (mixture of iron hematoxylin A and B solution in equal proportion) is stained for 10 min. 1% hydrochloric acid ethanol differentiation solution is stained with ponceau acid fuchsin dye solution for 10 min after differentiation, processed with phosphomolybdic acid solution for about 5 min, aniline blue dye solution is directly used to counter-stain for 5 min without water washing, and finally ethanol is used to dehydrate for three times, and xylene is transparent for three times.

Immunohistochemical Staining

The paraffin sections are deparaffinized to water and then the tissue sections are placed in an autoclave containing citrate antigen retrieval buffer (PH of 6.0) for antigen retrieval. 3% hydrogen peroxide solution is used (hydrogen peroxide:purified water=1:9) to block endogenous peroxidase, added with plus 3% BSA for blocking, then incubated with primary antibody overnight at 4° C. A secondary antibody of the corresponding species of the primary antibody is added and incubated at room temperature for 50 min, and the nuclei are stained with hematoxylin. After each incubation, cells are washed twice with PBS. The stained cells are photographed with a fluorescence microscope (NIKON ECLIPSE TI-SR).

The image analysis system is used to automatically read the section tissue measurement region, and respectively analyze and calculate the number of weak, medium and strong positive cells in the measurement region (negative: non-staining, counting 0 point; weak positive: light yellow, counting 1 point; medium positive: brown yellow, counting 2 points; strong positive: tan, counting 3 points). Histochemistry score (H-score) is calculated to reflect the degree of positive intensity.

$H\text{-score}=\Sigma(P_i \times i)=$(percentage of weak intensity cells×1)+(percentage of moderate intensity cells×2)+(percentage of strong intensity cells× 3), where $P_i$ represents positive cell ratio; $i$ stands for tint strength).

Synthesis of PTMC-b-PEG-b-PTMC and Characterization Results Thereof

Figure 2:
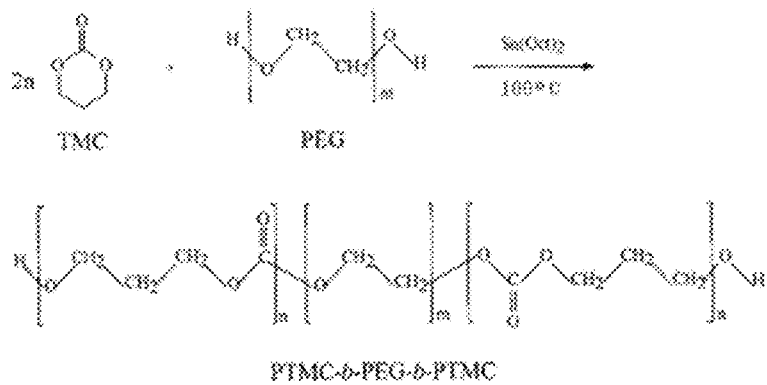
FIG. 2 is a schematic diagram of the synthesis process of a triblock copolymer of the present disclosure.

PTMC-b-PEG-b-PTMC triblock copolymers are synthesized by ring-opening polymerization of trimethylene carbonate initiated by polyethylene glycol hydroxyl groups (FIG. 2). Under the catalysis of $Sn(Oct)_2$, TMC is copolymerized with PEG to form PTMC-b-PEG-b-PTMC block copolymer. The copolymerization with different PEG block ratios and the physical properties of the product fractions are shown in Table 1.

The degradation rate and mechanical properties of block copolymers with different molecular weights are very different. Different feed ratios have a significant impact on the molecular weight of block copolymers. Implantation in the intestinal tract requires the products to have a suitable degradation rate and excellent mechanical properties. Therefore, this experiment focuses on the impact of different ratios of TMC monomer and PEG in the raw materials on the molecular weight and properties of block copolymer PTMC-b-PEG-b-PTMC. The factors of different mass ratios of TMC monomer to PEG in raw materials are studied, and the reaction time is controlled at 24 h. The results are shown in Table 1. The data show that as the proportion of PEG in the raw materials decreases, the intrinsic viscosity of PTMC-b-PEG-b-PTMC increases and the molecular weight increases.

Figure 3:
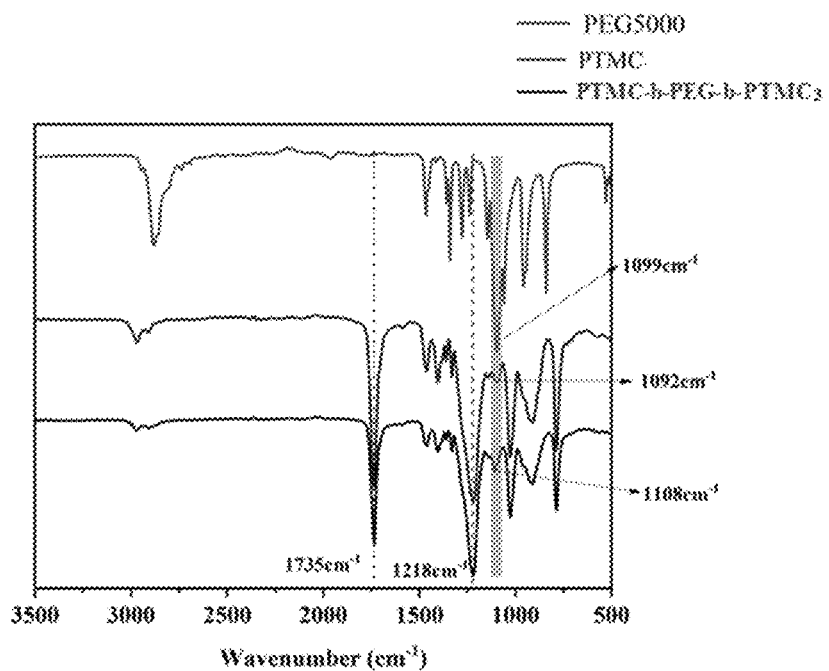
FIG. 3 is an infrared spectrum diagram of PTMC, PEG and the copolymer PTMC-b-PEG-b-PTMC.

FIG. 3 is an infrared spectrum diagram of PTMC, PEG and the copolymer PTMC-b-PEG-b-PTMC. The copolymer PTMC-b-PEG-b-PTMC overlaps with the characteristic absorption peaks of PTMC at 1735 $cm^{-1}$ and 1218 $cm^{-1}$, which are characteristic peaks of carbonate carbonyl and ether linkages, respectively. The characteristic absorption peak of PEG at 1099 $cm^{-1}$ and the characteristic absorption peak of PTMC at 1092 $cm^{-1}$ are the characteristic absorption peaks of C—O, and the relative intensity of the peak of copolymer PTMC-b-PEG-b-PTMC at 1108 $cm^{-1}$ is higher than that at 1092 $cm^{-1}$.

Figure 4:
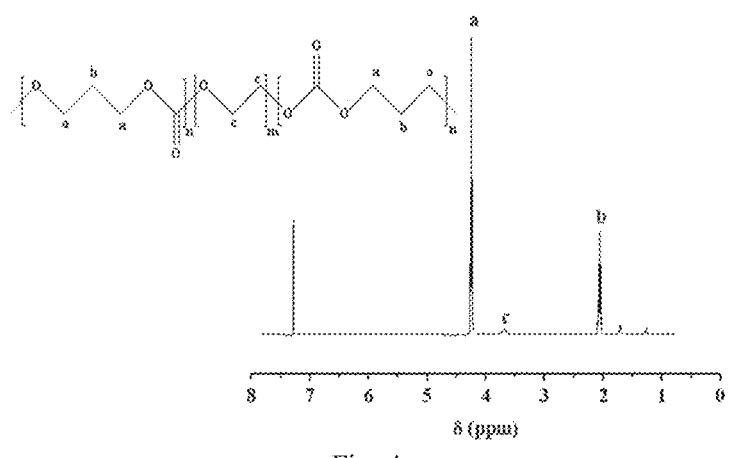
FIG. 4 is a $^1$H-NMR spectrum of the block copolymer PTMC-b-PEG-b-PTMC.

FIG. 4 is a $^1H$-NMR spectrum of the block copolymer PTMC-b-PEG-b-PTMC. It clearly shows that the chemical shift δ at 4.25 ppm (a) belongs to the methylene protons next to the oxygen in the PTMC block, δ at 2.06 ppm (b) belongs to the other methylene protons in the PTMC block, while δ at 3.68 ppm (c) belongs to the methylene protons in the PEG backbone.

The DSC data are listed in Table 1. The glass transition temperature is related to the composition of the copolymer, the mole fraction of PEG in the copolymer decreases from 50% to 0.5%, and the glass transition temperature increases from −30.88° C. to −19.48° C. The results show that the copolymer is in rubbery state at physiological temperature, which is suitable for implantation in vivo.

TABLE 2

Composition and molecular weight of PTMC-b-PEG-b-PTMC copolymer

Figure 5:
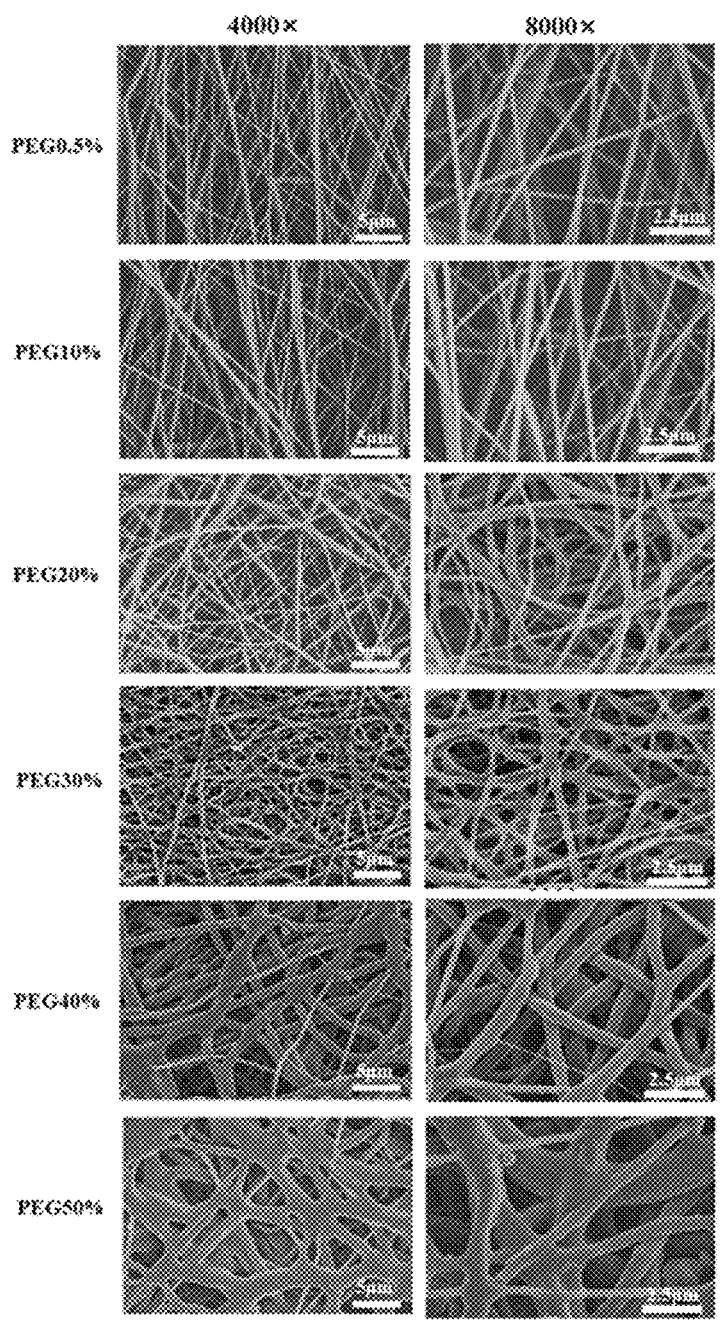
FIG. 5 is an SEM image of PEG-b-PTMC-b-PEG composite fiber with PEG percentages of 0.5%, 10%, 20%, 30%, 40%, and 50% relative to PTMC content.
Figure 6:
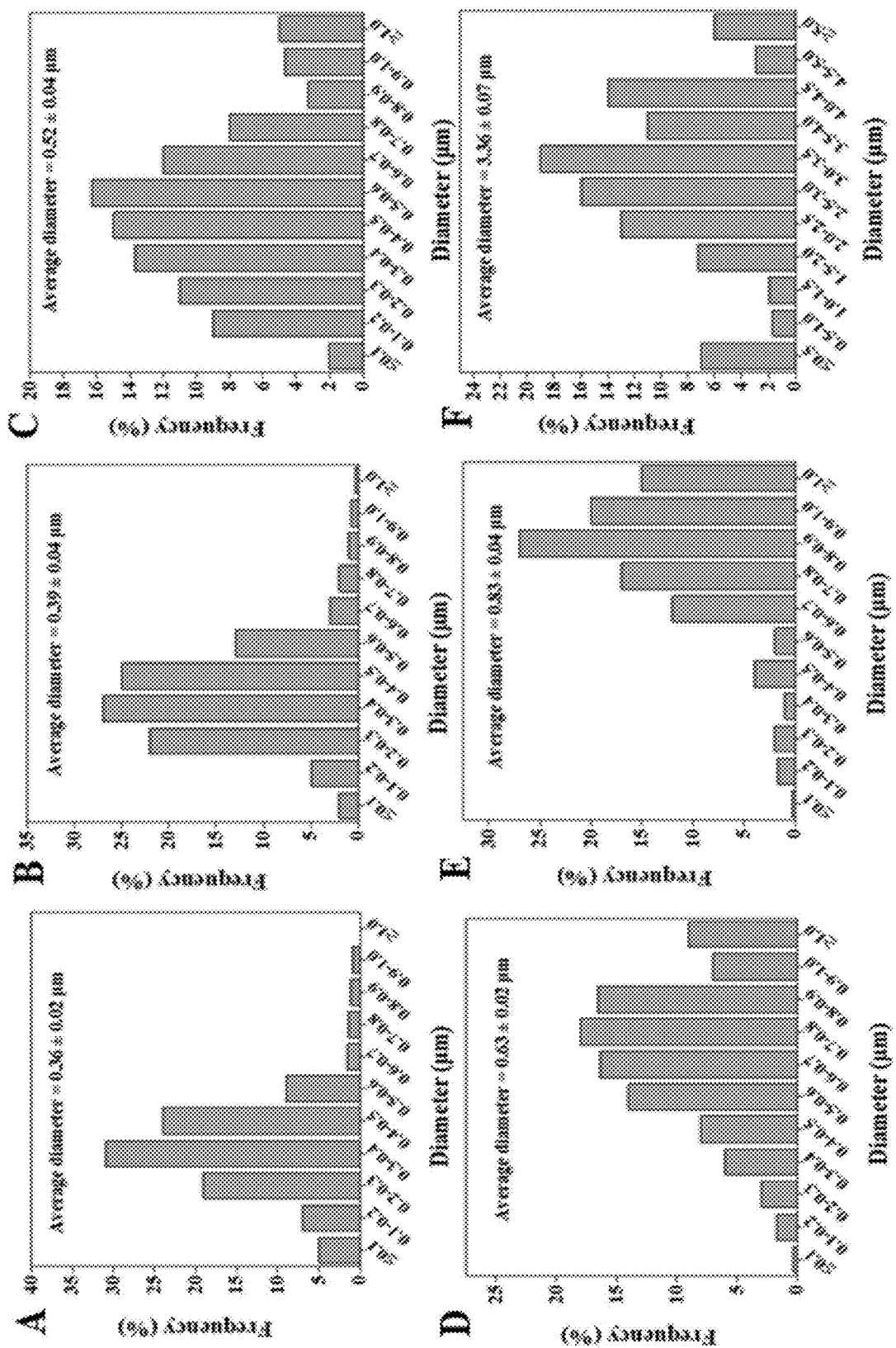
FIG. 6 is a fiber diameter distribution of PEG-b-PTMC-b-PEG fibers wherein a weight percent of PEG content relative to the PTMC is (A) 0.5%, (B) 10%, (C) 20%, (D) 30%, (E) 40% and (F) 50%.

| Samples ID | Sample name | PEG wt % | Mn ($10^3$) | [η] (dL/g) | Tg (° C.) |
|---|---|---|---|---|---|
| PTMC-PEG-PTMC$_1$ | PEG50% | 50 | 11.75 | 0.323 | −30.88 |
| PTMC-PEG-PTMC$_2$ | PEG40% | 40 | 14.45 | 0.370 | −27.22 |
| PTMC-PEG-PTMC$_3$ | PEG30% | 30 | 18.18 | 0.456 | −25.77 |
| PTMC-PEG-PTMC$_4$ | PEG20% | 20 | 26.66 | 0.599 | −23.39 |
| PTMC-PEG-PTMC$_5$ | PEG10% | 10 | 49.16 | 0.969 | −22.31 |
| PTMC-PEG-PTMC$_6$ | PEG0.5% | 0.5 | 102.97 | 1.733 | −19.48 | a. Determined by $[\eta] = KM^\alpha$, $K = 1.986 \times 10^{-4}$, $\alpha = 0.789$ Electrospun Fibers The morphology of electrospun fibers depends on various parameters including voltage, spinning flow rate, spinning distance, and solution properties such as viscosity, conductivity, and surface tension. To understand the effect of PEG block content on the microstructure of the samples, secondary electron scanning electron micrographs are obtained at different magnifications (FIG. 5). As the PEG block content increases from 0.4% to 50%, a gradual coarsening of the fiber diameter is observed. When the content of PEG exceeds 30%, the fiber adhesion increases, and the fiber begins to take on a non-uniform state. FIG. 6 shows an average fiber diameter and diameter distribution of the electrospun film. Similar average fiber diameters are detected when the PEG content is not higher than 20%. When the PEG content is further increased, the average fiber diameter increases and the difference in fiber diameters becomes larger, especially when the PEG content is 50%, and the average fiber diameter reaches 3.36 μm. The changes in the fiber adhesion phenomenon of 20% and 30% samples can be attributed to the instability of the jet in the electrospinning process. The stability of the electrospinning jet is affected by the properties of the spinning solution (such as viscosity and conductivity). The addition of PEG changes the viscosity and tension of the solution. In order to achieve a stable electrospinning jet, a balance between viscosity and tension is necessary. Table 3 summarizes the porosity of the electrospun fiber films. The obtained electrospun films have porosities from 72%±2% to 98%±2%, with PEG0.5% having the highest porosities as they have a relatively large pore size (FIG. 5) and a narrow and uniform distribution of fiber diameters (FIG. 6).

TABLE 3

Porosity of PTMC-b-PEG-b-PTMC fibers with different PEG contents

| Samples | PEG 0.5% | PEG 10% | PEG 20% | PEG 30% | PEG 40% | PEG 50% |
|---|---|---|---|---|---|---|
| Porosity | 98% ± 2% | 96% ± 1% | 90% ± 4% | 83% ± 1% | 77% ± 1% | 72% ± 2% |

Hydrophobicity of Copolymer

The good hydrophilicity of the material makes it more biocompatible, so in order to evaluate the hydrophilicity and hydrophobicity of PTMC-b-PEG-b-PTMC, a water contact angle of the sample surface is measured by dynamic contact angle experiment and is listed in Table 4. The results clearly show that the dynamic contact angle increases with decreasing PEG content in the copolymer, indicating that the hydrophilicity of the copolymer is proportional to the PEG content in the copolymer. The water contact angle (FIG. 7(A)) on the surface of the samples is measured every five minutes. The contact angle of all samples decrease with the increase of time, including hydrophobic samples, which indicates that the porous structure of electrospun material had good water absorption, and the change rate of contact angle increases with the increase of PEG content.

Figure 7:
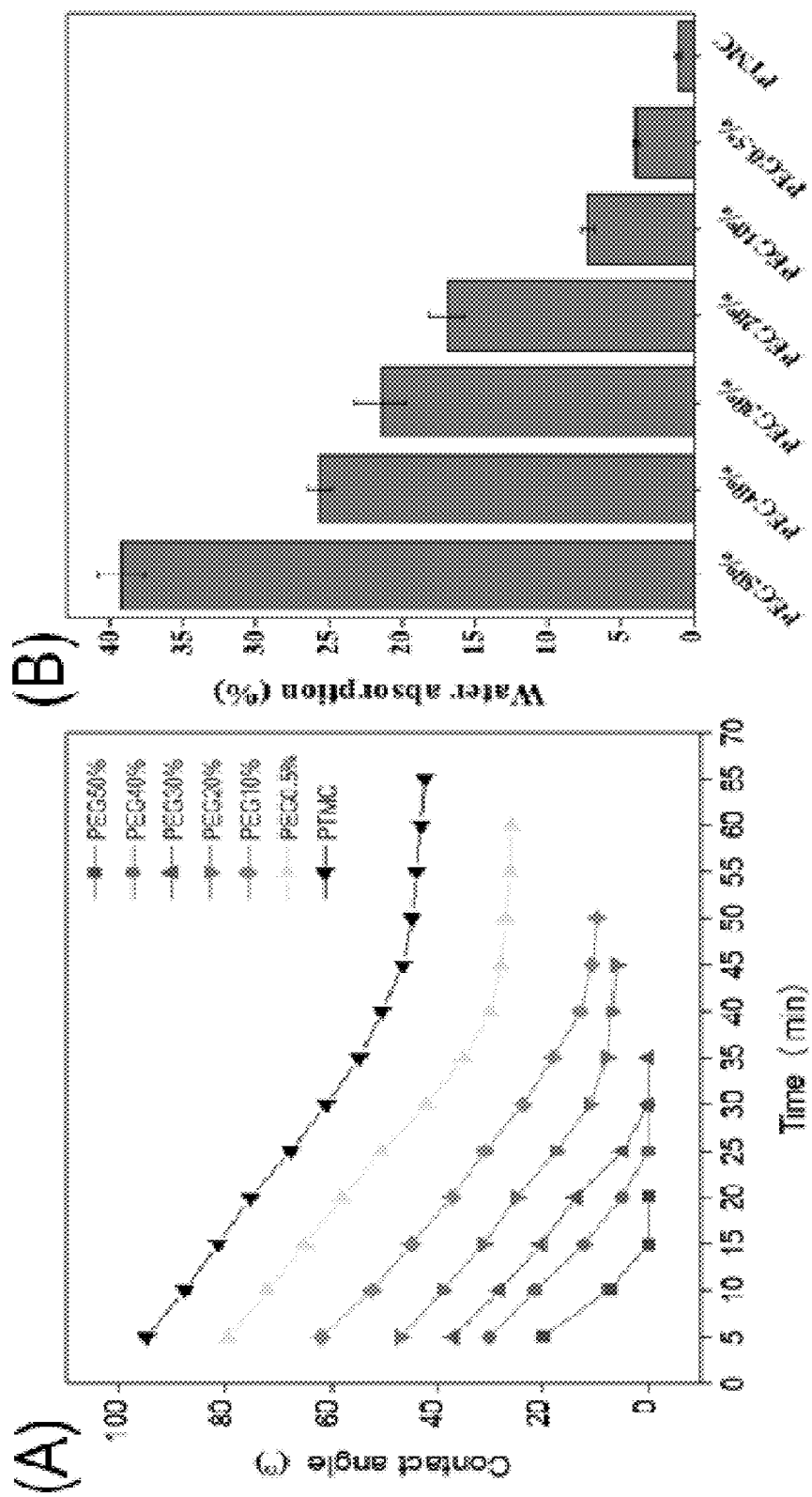
FIG. 7 shows the contact angle values as a function of time for different samples of triblock copolymer (A) and the water absorption for samples placed in PBS solution for 24 hours.

It can also be verified from the water absorption (FIG. 7(B)) that the high porosity of the fibrous stent and the addition of hydrophilic PEG greatly improved the water absorption of the stent. When the content of PEG exceeds 20%, the water absorption increases significantly.

TABLE 4

Advancing contact angles on PTMC-b-PEG-b-PTMC copolymers

| Samples | PEG 50% | PEG 40% | PEG 30% | PEG 20% | PEG 10% | PEG 0.5% | PTMC |
|---|---|---|---|---|---|---|---|
| Contact angle (°) | 19.95 | 30.07 | 36.85 | 46.73 | 61.83 | 79.45 | 84.92 |

Evaluation of Mechanical Properties of Electrospinning Samples

The proportions of PEG block also have a great influence on the mechanical properties of the material. The mechanical properties of anastomosis stents prepared by PTMC-b-PEG-b-PTMC electrospinning are listed in Table 5. The elastic modulus of the copolymer decreases from 29.76±0.47 MPa to 16.27±0.08 MPa with the decrease of PEG block ratio, while the tensile strength and elongation at break decrease. This is because PEG is a semi-crystalline micro-phase state, which has plasticizing and hardening effect on the stent. With the increase of PEG, the crystallinity of the material increased and the elongation at break decrease.

Figure 8:
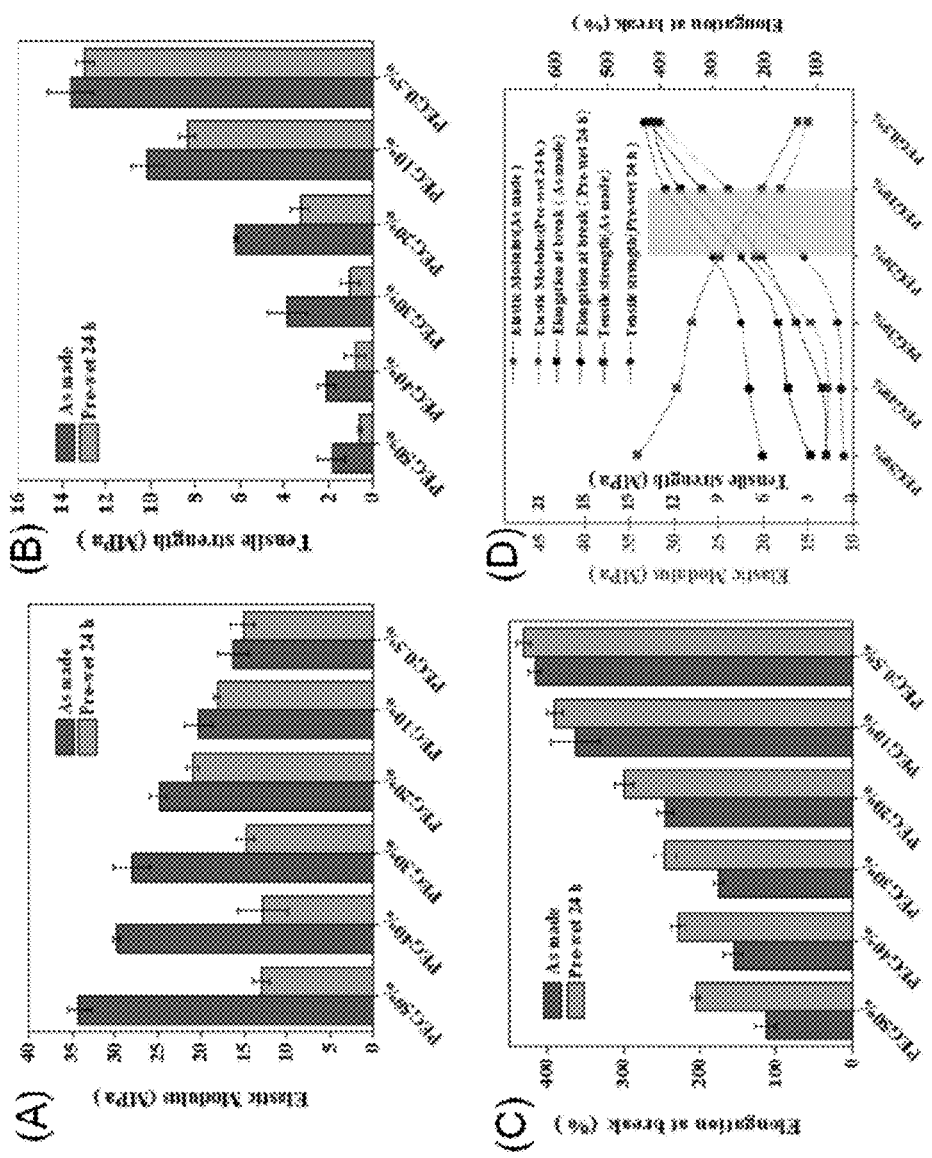
FIG. 8 shows the mechanical properties of electrospun intestinal anastomosis stents with different PEG contents before and after being placed in PBS solution; Changing trends of (A) elastic modulus, (B) tensile strength and (C) elongation at break, (D) mechanical properties.

The mechanical property of the stent material under physiological conditions is an important indicator of the implant material. In order to observe the mechanical property of the material under physiological conditions, the sample is soaked in PBS solution for 24 h before the test, and then the effect of the sample containing more than 20% PEG on the tensile strength and elastic modulus of the stent is tested. The elongation at break of the stents after the samples are soaked in PBS for 24 h increase to some extent (FIG. 8 (C)), which is caused by the further increase of hydrophilicity of the stents. When the content of PEG is more than 20%, the difference in the change of elastic modulus and elongation at break of the stent after water absorption is large (FIGS. 8 (A) and (B)), which indicates that the mechanical properties are not stable under physiological conditions, which is undesirable. The smaller the content of PEG, the smaller the difference between the mechanical properties in dry state and wet state. However, when the content of PEG is 0.5%, the stent has almost no hydrophilicity, which does not meet the original intention of designing intestinal anastomosis stent. In combination with the foregoing content, the mechanical properties of the material will be changed with the addition of PEG. In order to understand this trend macroscopically, we can visually see the influence and changing trend from FIG. 8 (D). In combination with the purpose, we believe that when the content of PEG is 10%-20%, its mechanical properties and hydrophilicity meet the requirements for implantation. In this range, the anastomosis stent has certain hydrophilicity, and has stable mechanical properties in dry and wet state, maintains certain mechanical strength and also has excellent flexibility, which ensures that it meets the strength without foreign body sensation and discomfort, and can be used as a good load-bearing repair tissue in intestinal trauma.

TABLE 5

Mechanical behavior of PTMC-b-PEG-b-PTMC copolymer

| Sample Name | $WA^a$ (%) | $E^b$ (MPa) | $E^c$ (MPa) | $T^d$ (MP) | $T^e$ (MPa) | $EB^f$ (%) | $EB^g$ (%) |
|---|---|---|---|---|---|---|---|
| PEG 50% | 39.28 | 34.09 | 12.97 | 1.86 | 0.60 | 112.47 | 204.55 |
| PEG 40% | 25.60 | 29.76 | 12.83 | 2.11 | 0.78 | 155.21 | 228.03 |
| PEG 30% | 21.47 | 28.03 | 14.77 | 3.85 | 1.02 | 173.56 | 245.29 |
| PEG 20% | 16.89 | 24.93 | 20.93 | 6.18 | 3.29 | 244.66 | 298.54 |
| PEG 10% | 7.24 | 20.31 | 18.12 | 10.17 | 8.37 | 362.15 | 389.57 |
| PEG 0.5% | 3.91 | 16.27 | 15.09 | 13.61 | 12.96 | 415.31 | 430.76 |
| Cecum | — | — | 5.02 | — | 0.74 | — | 31.24 |

$^a$water absorption,
$^b$elastic modulus (as received),
$^c$elastic modulus (pre-wet for 24 h),
$^d$tensile strength (as received),
$^e$tensile strength (pre-wet for 24 h)
$^f$elongation at break (finished product),
$^g$elongation at break (pre-wet for 24 h)

Based on the comprehensive factors of hydrophilicity, mechanical properties and in vitro enzymatic degradation, we believe that when the content of PEG is within 10%~20%, the comprehensive properties of stent are consistent with our expectations. In this study, the rat caecum is implanted with a sample of 15% PEG as an anastomosis stent to observe the subsequent degradation and healing promotion in vivo. Therefore, we select the samples with this PEG content for electrospinning to study the influence of samples with different thickness obtained under different electrospinning parameters on the mechanical properties.

Study on Influence of Samples with Different Thickness Obtained Under Different Electrospinning Parameters on the Mechanical Properties Based on the comprehensive factors of hydrophilicity, mechanical properties and in vitro enzymatic degradation, we believe that when the content of PEG is within 10%~20%, the comprehensive properties of stent are consistent with our expectations. In this study, the rat caecum is implanted with a sample of 15% PEG as an anastomosis stent to observe the subsequent degradation and healing promotion in vivo. Therefore, we select the samples with this PEG content for electrospinning to study the influence of samples with different thickness obtained under different electrospinning parameters on the mechanical properties.

The dried sample is dissolved in a mixed solution of chloroform/DMF (9/1, V/V) to prepare a solution with a concentration of 5.5%, and placed on a shaker at 37° C. for 36 h to sufficiently dissolve the sample, so as to obtain a uniform co-dissolved spinning stock solution. The stock solution is loaded into a 2.5 ml of syringe comprising a metal needle with an internal diameter of 0.5 mm. The specific electrospinning conditions are detailed in Table 1. The sample thickness after spinning is determined by the specific electrospinning time. The resulting fibers are further dried in a vacuum drying oven at room temperature for 24 hours to remove residual organic solvents and moisture. The spun samples are used for mechanical property testing as well as in vitro degradation testing.

Electrospinning Conditions

| Needle pushing speed | Distance from needle to receiver | Rotation speed of roller | Voltage | Temperature | Humidity |
|---|---|---|---|---|---|
| 0.5~2.5 mL/h | 20 cm | 200~400 RPM | 15 V | 35° C. | 25% |

| Needle pushing speed/ $mL \cdot h^{-1}$ | Rotation speed of roller/ RPM | Electrospinning time/h | Thickness of anastomosis tube/mm | Elastic Modulus/MPa | Elongation at break/% |
|---|---|---|---|---|---|
| 1.0 | 350 | 3 | 0.05 | 4.67 | 76.1 |
| 2.0 | 200 | 4 | 0.10 | 9.82 | 128.7 |
| 0.7 | 350 | 10 | 0.15 | 16.53 | 264.2 |
| 1.5 | 270 | 12 | 0.2 | 21.57 | 409.3 |
| 2.5 | 300 | 10 | 0.25 | 23.81 | 423.9 |
| 2.0 | 220 | 15 | 0.30 | 25.02 | 440.6 |

In Vitro Biodegradation Evaluation

The hydrophilicity of a polymer has an important influence on its degradation behavior and bio-compatibility. Due to the slow degradation rate of PTMC homopolymer, copolymerization of TMC with PEG, lactones and lactic acid has become an effective way to improve the degradation performance of PTMC, which greatly expands the application range of PTMC as medical materials. The introduction of hydrophilic block on the hydrophobic backbone can accelerate the penetration of $H_2O$ into the matrix, which is a simple and effective method to improve the degradation rate. Ptmc-b-PEG-b-PTMC copolymers containing hydrophilic PEG blocks synthesized herein have better degradation properties than PTMC homopolymers.

It has been reported in the literature that PTMC is degraded mainly by in vitro enzymolysis and in vivo surface erosion. PTMC is inert in PBS solution, and the change of mass and relative molecular mass is very little. The weight loss rate of PTMC in enzyme solution is much greater than that in hydrolysis. The stability of PTMC in PBS solution and the rapid degradation in lipase solution indicate that lipase participates in the degradation reaction. Both Zhang etc. and Yang etc. believe that the enzyme acts as an interfacial activation that accelerates the rate at which the degraded product is lost to solution. Based on the surfactant effect of lipase in the diffusion of degradation products, PTMC has high in vitro enzymatic degradation rate, so in vitro enzymatic degradation is focused on. It has been widely reported that the shape of the copolymer has a great influence on the degradation. As an intestinal stent, we studied the degradation properties of the film-like material after electrospinning.

Figure 9:
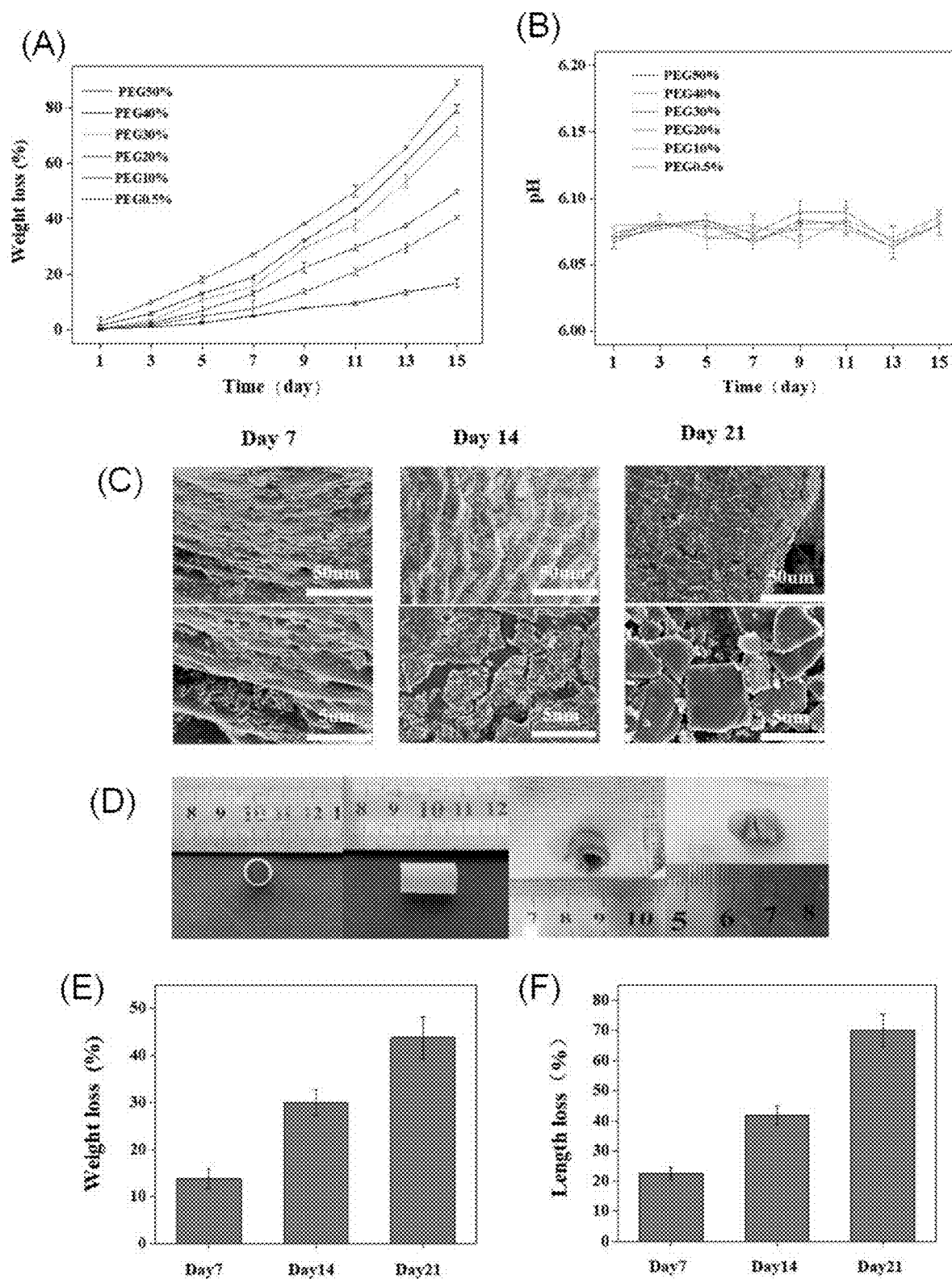
FIG. 9 shows (A) the weight loss of PTMC-b-PEG-b-PTMC in vitro enzymatic degradation as a function of degradation time, (B) the pH curves of lipase solutions after enzymatic degradation of PTMC-b-PEG-b-PTMC films with different molecular weights, (C) the degradation in vivo at different times, (D) the comparison of anastomosis stents before and after implantation, (E) the weight loss and (F) the length loss of anastomosis stents removed from rats at corresponding times.

The effect of enzyme on weight loss rate is studied (FIG. 9 (A)). The experimental results show that the hydrophilicity of block copolymer PTMC-b-PEG-b-PTMC increases and the degradation is accelerated with the increase of PEG ratio. The pH of the lipase solution is 6.08 and change in the pH of the solution during degradation is observed with little change (FIG. 9 (B)).

As an intestinal anastomosis stent, it is considered suitable to have good hydrophilicity and appropriate degradation rate under the premise of satisfying its mechanical properties. The stents with high PEG content have good hydrophilicity, but the degradation rate is too fast, and the crystallization zone significantly affects the mechanical properties of the stents, and the mechanical properties become unstable after water absorption. When the content of PEG is 10%-20%, the stent has excellent and stable mechanical properties, meets the requirements of complex intestinal environment, and its degradation rate is moderate, which can reach 40%~50% degradation in two weeks. The certain hydrophilicity also makes it have good biocompatibility.

The object of this animal experiment is male SD rats, and the intestinal healing period of rats is about 14 days. Therefore, the anastomosis stent implanted in the intestinal tract should meet the requirements of mechanical strength for at least two weeks and degradation for about three weeks. Based on the difference between intestinal environment and in vitro enzyme solution, the degradation rate of material in physiological environment is lower than that of enzyme solution. There is no quantitative data on the relationship between the degradation rate of material and enzyme solution. According to our previous experiments, the degradation rate of in vitro enzyme will be slightly faster than that of in vivo enzyme solution. Based on the comprehensive factors of hydrophilicity, mechanical properties and in vitro enzymatic degradation, we believe that when the content of PEG is within 10%~20%, the comprehensive properties of stent are consistent with our expectations. In this study, the rat caecum is implanted with a sample of 15% PEG as an anastomosis stent to observe the subsequent degradation and healing promotion in vivo.

Microscopic morphology is observed after removal of the in vivo anastomosis stent at the corresponding time point (FIG. 9 (C)). Both the mass and the length of the anastomosis stent are reduced to varying degrees (FIGS. 9 (E), (F)), with a mass reduction of more than 40% after 21 days and a length reduction of 70%, namely, the length reduction rate is larger than the mass reduction rate, which may be due to the material absorbing water. After in vivo degradation, the morphology had already started to disintegrate, but the macroscopic integrity remains better (FIG. 9 (D)), still with some support. After 28 days the rat cecum is dissected and no anastomosis stent is found, presumably after 21 days stent disintegration accelerates with intestinal waste metabolism or mechanical properties is insufficient to support the intestine and then it exits from the surgical suture. Either way, however, the stent mees the requirement to protect the anastomosis for at least two weeks in vivo, so we consider a material with a PEG content of 15% excellent in terms of degradation.

In Vitro Biological Evaluation
Antibacterial

It is well known that the wound healing process may be infected with bacteria, which will delay wound healing. There are numerous microorganisms and bacteria in the intestinal tract, with the number of bacteria reaching the order of $10^{14}$ and more than 1000 species. Compared with other epithelia, the intestinal healing faces a higher density of pathogenic bacteria, which will disturb the normal physiological process of wound healing. Due to the particularity of surgical site, it is difficult to maintain a relatively clean environment for intestinal anastomosis, and the antibacterial and bacterial isolation effect of anastomosis stent plays a very important role.

Figure 10:
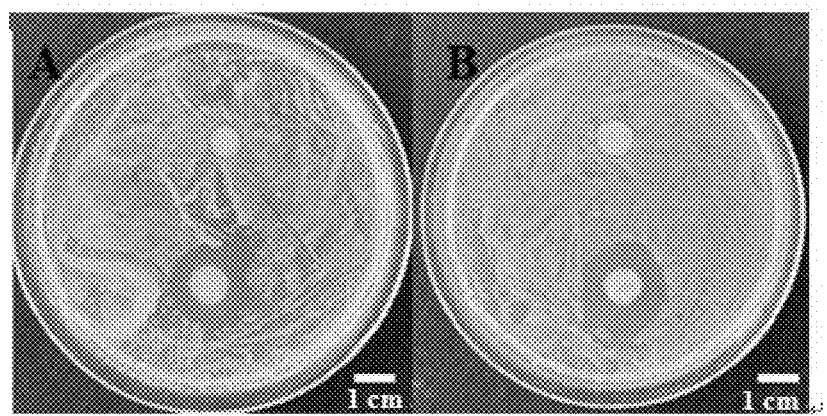
FIG. 10 shows the antibacterial effect of triclosan-free samples (top panel) and triclosan-containing samples (bottom panel), A represents *Staphylococcus aureus*, B represents *Escherichia coli*, with scale bar of 1 cm.

To address this issue, the antimicrobial agent, triclosan, is added to the sample in a proportion to render the material antimicrobial to ensure relative cleanliness of the wound site. As shown in FIG. 10, the sample without triclosan does not resist bacteria, and the sample with triclosan added has significant zones of inhibition against *Pseudomonas aeruginosa, Escherichia coli* and *Staphylococcus aureus*. Since PTMC-b-PEG-b-PTMC degradation is a surface erosion degradation and a degradation process gradually deep into the interior from the surface, triclosan can be slowly released and always play a bactericidal role.

Hemolysis Rate

Figure 11:
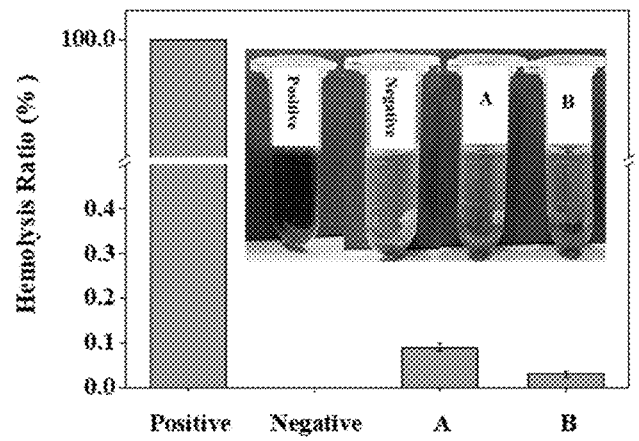
FIG. 11 shows the hemolysis rates of different materials: (A) PTMC-b-PEG-b-PTMC copolymer experimental group, (B) TCS/PTMC-b-PEG-b-PTMC copolymer experimental group.

Since the anastomosis stent is in direct contact with the site of intestinal anastomosis, if the material causes the rupture of red blood cells, it often causes adenosine diphosphate to be released, accelerating platelet aggregation and thus triggering thrombosis. Hemolysis of anastomosis stents is assessed by direct contact of in vitro materials with blood, and the experimental results are shown in FIG. 11, where the hemolysis rate is less than 0.1%, well below the upper limit of 5% for implantable medical devices. The introduction of PEG as a hydrophilic moiety enables the material to form a "water film" upon contact with moisture. Such an aqueous layer effectively prevents direct contact of the red blood cells with the hydrophobic substrate, thereby minimizing the problem of red blood cell rupture caused by the material itself.

Cytotoxicity

Figure 12:
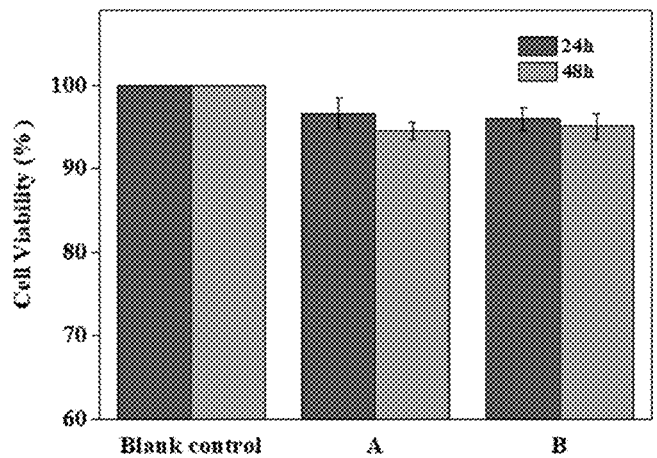
FIG. 12 is a graph of the cytotoxic effect of samples with A being the PTMC-b-PEG-b-PTMC copolymer group and B being the TCS/PTMC-b-PEG-b-PTMC copolymer group.

L929 cells are used for in vitro experiments of cytotoxicity and cytocompatibility to evaluate the cytocompatibility of pure PTMC-b-PEG-b-PTMC with triclosan added PTMC-b-PEG-b-PTMC (FIG. 12). The L929 cells are incubated with the samples for 24 h and 48 h, and the cytotoxicity values of the samples added with triclosan are similar to those of the simple block copolymer, and the cell survival rates are all maintained above 90%, which indicated that the addition of triclosan is effective and feasible, and could not cause damage to the tissue cells while achieving bactericidal effect.

Wound Recovery Evaluation
Abdominal Adhesion Score and Anastomotic Burst Pressure The healing of intestinal anastomosis is mainly through inflammatory reaction, cell proliferation, intestinal wall structure reorganization, and so on to achieve mechanical, histological and functional repair for ultimate healing. Functional repair is a rather lengthy process involving digestive absorption, endo- and extra-secretion, nerve repair and transitional complex movement, so mechanical and histological indicators must be achieved before we consider the anastomotic site to complete healing. In combination with the operation of surgery, the following indicators shall be achieved in the animal experiment stage: burst pressure experiment—an indicator of mechanical healing; abdominal adhesion score-response to local inflammatory conditions near the anastomosis; HE staining, masson staining and immunohistochemical staining of anastomotic tissues—to evaluate the degree of inflammatory cell infiltration and collagen deposition.

Figure 13:
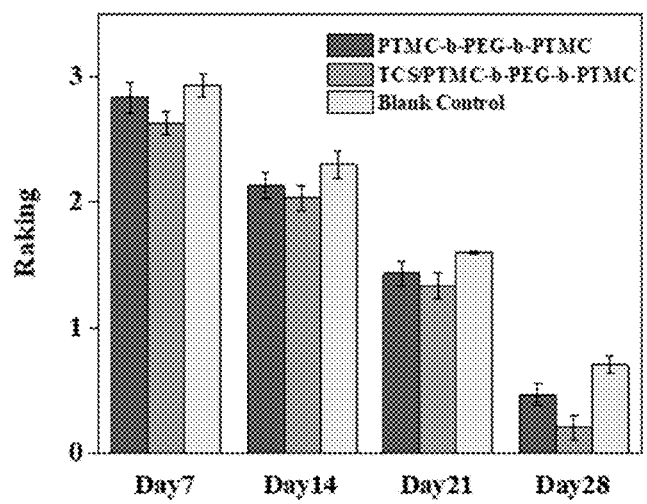
FIG. 13 shows abdominal adhesion scores at various times after intestinal anastomosis.
Figure 14:
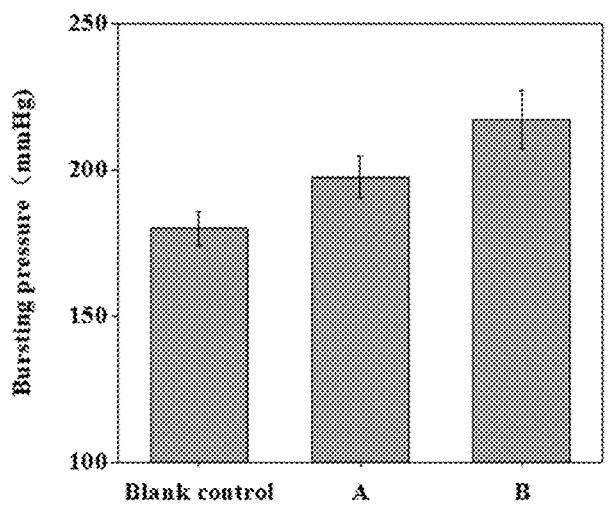
FIG. 14 shows the anastomotic burst pressure of different sample groups 7 days after surgery, A is PTMC-b-PEG-b-PTMC group, and B is TCS/PTMC-b-PEG-b-PTMC group.

Laparotomy is respectively performed on the 7th, 14th, 21th and 28th day after surgery, and the abdominal adhesion is scored, for which see FIG. 13 for details. When the abdominal cavity is irritated or infected due to injury, the local area produces a gelatinous fluid of fibrinogen, which is quickly transformed into fibrin clot and covers the mucosal surface of the wound, providing repair protection. Fibrin has a high degree of adhesion that allows the abdominal mucosa to be held close to each other. After the wound heals, there is no trace if the body absorbs the fibrin well. In case of incomplete absorption, adhesions may persist and in severe cases may become adhesive ileus, affecting normal physiological activities of the intestinal tract. The anastomosis stent-assisted healing group has significantly less adhesion than the control group, because the anastomosis stent effectively blocks the direct contact between the wound and intestinal contents, reduces the occurrence of infection, so that the anastomotic stoma has better repair and healing speed.

The burst pressure of anastomotic stoma can effectively reflect the firmness of anastomotic site healing after intestinal anastomosis for a period of time, and the mechanical index can quantitatively reveal the amount of tension the anastomotic stoma can endure. The balance between the deposition of submucosal collagen synthesis and the rate of remodeling is a critical factor in the process of intestinal healing. Insufficient and excessive tissue repair can affect normal bowel function, insufficient repair can result in ulcers and fistulas, and excessive repair can result in fibrosis and stenosis. The remodeling rate of collagen is much higher than the deposition rate in the first 4 days after surgery, and collagen deposition is dominant from the 5th day after surgery, and finally reached the peak of proliferation phase in the 7th day. Delay or damage to the peak of the proliferative phase can lead to anastomotic dehiscence. Over-deposition and inflammation of collagen can lead to anastomotic strictures. Therefore, on the 7th postoperative day, without affecting the local anastomotic site, the adhesions are separated, then the operative segment cecum is obtained and the burst pressure experiment of the anastomotic cecum segment is performed (FIG. 13). Burst pressure of 20 surviving rats in control group is 183 mmHg, which is lower than 197.6 mmHg (PTMC-b-PEG-b-PTMC group) and 217.3 mmHg (TCS/PTMC-b-PEG-b-PTMC group)PTMC-b-PEG-b-PTMC group) of the 20 surviving rats in intestinal anastomosis stent group. The anastomosis stent significantly promotes wound healing, and the addition of triclosan reduces bacteria at the wound site, which is beneficial to wound healing. There is statistical difference among the three groups ($P<0.001$).

Histological Analysis

During acute and chronic intestinal inflammation, macrophages and neutrophils induce local tissue damage by secreting reactive oxygen radicals and tissue degrading enzymes. If tissue damage is severe, myofibroblasts can migrate to the defect site. Inflammation is associated with the infiltration of immune cells, such as T cells, macrophages and neutrophils, which also often cause severe damage to the tissue in which inflammation occurs. This persistent inflammation may thus lead to the formation of fibrosis and stenosis.

Figure 15:
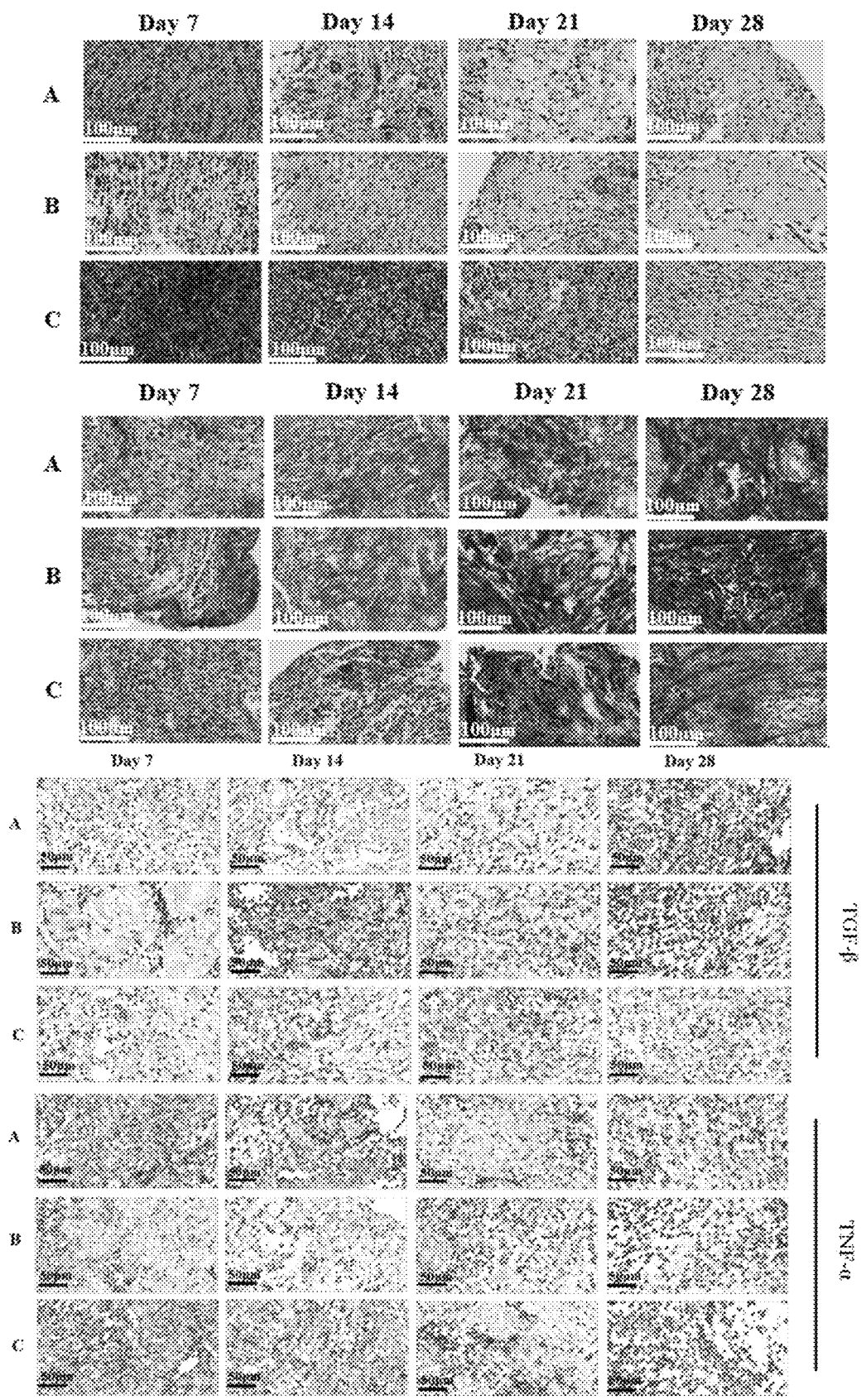
FIG. 15 shows H&E and Masson staining of intestinal wall tissue near the anastomosis.

At the corresponding time points after surgery, we performs H&E and Masson staining of the intestinal wall tissue near the anastomosis (FIG. 15). In chronological order, the tissue healing process can be divided into inflammatory phase, proliferation phase and remodeling phase, and the three processes are not strictly defined. In general, day 7 is the node between the inflammatory phase and the proliferative phase, and day 14 is the node between the proliferative phase and the remodeling phase. The inflammatory phase is characterized by the accumulation and infiltration of neutrophil-dominated inflammatory cells. In proliferative phase, the number of fibroblasts is increased, and the number of poorly organized collagen fibers is increased. In remodeling phase, the acute inflammation is significantly reduced. Instead, the chronic inflammation is marked by the production of multinucleated giant cells, and the collagen fibers are significantly increases. HE staining can show the degree of inflammatory cell infiltration. At the corresponding time points after surgery, the inflammatory cell infiltration in the control group is significantly higher than that in the stent-assisted group, and the inflammatory cell infiltration in the stent-assisted group with triclosan is significantly less than that in the stent-assisted group without triclosan. Masson staining also verifies the foregoing regulation, in which the stent group reduces the inflammatory reaction due to the exclusion of bacteria, which facilitates the regeneration of fibers, while the addition of triclosan further promotes wound healing.

Immunohistochemical Analysis

Wound repair is accomplished by growth factors secreted by cells, such as transforming growth factor-$\beta$ (TGF-$\beta$). TGF-$\beta$ is the most potent and important inducer of $\alpha$-smooth muscle actin ($\alpha$-SMA). TGF-$\beta$ is increased in myofibroblasts at sites of fibrosis in patients with experimental enterocolitis and Crohn's disease. Transforming growth factor can induce the expression of type i collagen, and can effectively stimulate the expression of $\alpha$-SMA. In the early stage of wound formation, TGF-$\beta$ is produced in large quantity. However, the continuous high level of TGF-$\beta$ may lead to excessive accumulation of collagen fibers at the wound site to form fibrosis, so as to gradually decrease the level of TGF-$\beta$ as the wound heals. The detection of TGF-$\beta$ level at the wound site can intuitively understand how fast and how well the wound recovers.

Since wound infection is one of the major causes of death in injured patients, tumor necrosis factor-$\alpha$ (TNF-$\alpha$) is chosen as a monitoring indicator to test the efficacy of anastomosis stents in preventing infection by immunohistochemical analysis. TNF-$\alpha$ is a cytokine that can directly kill tumor cells without obvious toxicity to normal cells, that is to say, it can promote T cells to produce various inflammatory factors, thereby promoting the occurrence of inflammatory response. Higher levels of TNF-$\alpha$ are detected if there is a significant amount of inflammation in the tissue.

CONCLUSION

The healing of the intestine after anastomosis is a complex and lengthy physiological process. In fact, intestinal anastomosis consists of three processes: physical healing, histological healing and physiological healing. Physical healing means that after anastomosis, the intestinal cavity can be closed, intestinal contents can not enter the abdominal cavity, intestinal wall can bear certain pressure. Histological healing means that the mucosal layer of the anastomosis is histologically united. The intestinal tract at both ends of the anastomotic stoma regains its original innervation, achieving integrated and orderly intestinal contraction and peristalsis, a process called physiological healing. The 7-week burst pressure results confirm that the implantation of anastomosis stent promoted the physical healing of anastomosis, and the results of Masson staining show that the anastomosis stent group has better collagen formation and could promote the histological healing of anastomosis.

Tension at the anastomosis is a major cause of poor healing. This tension may come from the tissue or may result from insufficient blood supply to the constantly tight vessels. The intestinal anastomosis stent prepared in this experiment has tissue flexibility, which can greatly relieve this tension, so that the anastomosis will have a better healing effect. Secondly, the anastomosis stent can effectively exclude the adverse factors such as bacteria and viruses, and create a relatively clean environment for the wound, which conclusion is essential for the healing of anastomotic stoma, which is proved by H&E staining, TGF-β and TNF-α.

Instructions for each technician: although the present disclosure has been described with reference to the foregoing specific embodiments, the inventive concept is not limited to this disclosure, and any modifications using the inventive concept are intended to be included within the scope of the patent claims.

The foregoing description is only a preferred embodiment of the present disclosure, and the scope of the present disclosure is not limited to the above-mentioned embodiments, and all the technical solutions falling within the idea of the present disclosure fall within the scope of protection of the present disclosure. It should be noted that a person of ordinary skill in the art would have been able to make several improvements and modifications without departing from the principles of the present disclosure, and these improvements and modifications are also considered to be within the scope of the present disclosure.

The invention claimed is:

1. A bioflexible elastomer intestinal anastomosis stent based on poly(trimethylene carbonate)-b-polyethylene glycol-b-poly(trimethylene carbonate) (PTMC-b-PEG-b-PTMC) triblock copolymer, wherein the intestinal anastomosis stent is integrally made of a PTMC-b-PEG-b-PTMC triblock copolymer synthesized by a ring-opening polymerization method of molecular medical materials of polytrimethylene carbonate (PTMC) and polyethylene glycol (PEG); a content of PEG in the PTMC-b-PEG-b-PTMC triblock copolymer is 10%-20% by weight; a thickness of the intestinal anastomosis stent is 0.05-0.3 mm; the intestinal anastomosis stent is of a gapless sleeve-inlaid structure comprising an inner tube of plant cellulose material and an outer sleeve of the PTMC-b-PEG-b-PTMC triblock copolymer material; and the stent is degraded in vivo for 2-3 weeks, and the inner tube of plant cellulose material is decomposable in vivo after 15-30 minutes.

2. The bioflexible elastomer intestinal anastomosis stent according to claim 1, wherein the outer sleeve of PTMC-b-PEG-b-PTMC triblock copolymer is loaded with triclosan (TCS).

3. A method of preparing the bioflexible elastomer intestinal anastomosis stent of claim 1, comprising the following steps:
(1) ring-opening polymerization of PTMC-b-PEG-b-PTMC: transferring PEG and trimethylene carbonate (TMC) monomers into a reaction vessel, dissolving catalyst Sn (Oct)$_2$ in an anhydrous toluene solution under a N$_2$ atmosphere, adding 100 ppm to the reaction vessel with a pipette to ensure copolymerization of the PEG and TMC monomers under anhydrous and oxygen-free conditions to form the PTMC-b-PEG-b-PTMC triblock copolymer, dissolving a product after 24 h to form a polymer solution, and purifying the polymer solution after complete dissolution of the product, repeating for multiple times to obtain a purified PTMC-b-PEG-b-PTMC triblock copolymer, and drying the purified PTMC-b-PEG-b-PTMC triblock copolymer in a vacuum drying oven for 48 h to form a dried purified PTMC-b-PEG-b-PTMC triblock copolymer, and then storing the dried purified PTMC-b-PEG-b-PTMC triblock copolymer in a drying cabinet;
(2) preparation of the bioflexible elastomer intestinal anastomosis stent by electrospinning: dissolving the dried purified PTMC-b-PEG-b-PTMC triblock copolymer in a DMF/THF mixed solution to form a prepared solution having a concentration of 5-10.0 wt %, adding 0.1-1.0 wt % of an antibacterial agent into the prepared solution; after mixing, placing the prepared solution on a shaker at 37° C. for sufficient dissolution to obtain a uniform co-dissolved spinning stock solution; loading the uniform co-dissolved spinning stock solution into a 2.5 ml syringe comprising a metal needle with an inner diameter of 0.5 mm, electrospinning the uniform co-dissolved spinning stock solution to form a fibre having a thickness of 0.2±0.01 mm; and further drying the fibre in the vacuum drying oven at room temperature to remove residual organic solvents and moisture.

4. The method according to claim 3, wherein in the step (1) and relative to a total weight, the TMC monomer is 70-90 wt %, the PEG is 5-29 wt %, and the catalyst Sn (Oct)$_2$ is 1-5 wt %.

5. The method according to claim 3, wherein in the step (1), copolymerization of the PEG and TMC monomers is at a temperature of 100-150° C. for 24-48 h.

6. The method according to claim 3, wherein in the step (1) dissolving the product after 24h to form the polymer solution comprises dissolving the product CHCl$_3$ or DMF or THF and shaking on a shaker being set at 37° C.

7. The method according to claim 3, wherein in the step (1), purifying comprises pouring the polymer solution into n-hexane or ethanol and continuously stirring with a glass rod.

8. The method according to claim 3, wherein in the step (2), the DMF/THF mixed solution comprises DMF:THF at 1:1 by weight.

9. The method according to claim 3, wherein in the step (2), a plant cellulose tube sleeve of a certain size is sheathed on an electrospinning receiver for spinning, and electrospinning the uniform co-dissolved spinning stock solution comprises forming the fibre on the plant cellulose tube sleeve at a needle pushing speed of 1.0-5.0 ml/h, a rotation speed of a roller of 100-500 RPM, a temperature of 25-35° C., and a humidity of 20-40%.

10. The bioflexible elastomer intestinal anastomosis stent according to claim 1, wherein the stiffness of the inner tube of plant cellulose material is greater than that of the outer sleeve of PTMC-b-PEG-b-PTMC triblock copolymer.

11. The bioflexible elastomer intestinal anastomosis stent according to claim 1, wherein the outer sleeve of PTMC-b-PEG-b-PTMC triblock copolymer comprises fibers of the PTMC-b-PEG-b-PTMC triblock copolymer.

12. The bioflexible elastomer intestinal anastomosis stent according to claim 1, wherein the outer sleeve of the PTMC-b-PEG-b-PTMC triblock copolymer has a porosity of at least about 90±4%.

13. The bioflexible elastomer intestinal anastomosis stent according to claim 11, wherein the fibers of the PTMC-b-PEG-b-PTMC triblock copolymer have an average diameter of less than about 0.83±0.04 μm.

14. The bioflexible elastomer intestinal anastomosis stent according to claim 1, wherein the outer sleeve of PTMC-b-PEG-b-PTMC triblock copolymer has an elastic modulus of less than about 25 MPa after soaked in saline for 24 hours.

15. The bioflexible elastomer intestinal anastomosis stent according to claim 11, wherein the fibers are adhered to the inner tube of plant cellulose material.

16. The bioflexible elastomer intestinal anastomosis stent according to claim 11, wherein the fibers are formed by electrospinning the PTMC-b-PEG-b-PTMC triblock copolymer onto the inner tube of plant cellulose material.

* * * * *